United States Patent [19]

Messina et al.

[11] Patent Number: 4,554,143

[45] Date of Patent: Nov. 19, 1985

[54] CRYSTALLINE FERROALUMINOPHOSPHATES

[75] Inventors: Celeste A. Messina, Ossining; Brent M. Lok, New City; Edith M. Flanigen, White Plains, all of N.Y.

[73] Assignee: Union Carbide Corporation, Danbury, Conn.

[21] Appl. No.: 514,335

[22] Filed: Jul. 15, 1983

[51] Int. Cl.$^4$ .................. C01B 25/45; B01J 27/18
[52] U.S. Cl. ................... 423/306; 502/150; 502/162; 502/164; 502/213
[58] Field of Search .............. 423/305, 306, 326; 502/162, 164, 208, 213, 214

[56] References Cited

U.S. PATENT DOCUMENTS

| | | | |
|---|---|---|---|
| 4,208,305 | 6/1980 | Kouwenhoven et al. | 423/326 |
| 4,310,440 | 1/1982 | Wilson et al. | 502/208 |
| 4,337,173 | 6/1982 | Otake | 502/208 |
| 4,372,930 | 2/1983 | Short et al. | 423/326 |
| 4,385,994 | 5/1983 | Wilson et al. | 210/689 |
| 4,440,871 | 4/1984 | Lok et al. | 502/214 |
| 4,500,651 | 2/1985 | Lok et al. | 502/208 |

OTHER PUBLICATIONS

"Dimensions of Phosphates", Proc. Int. Congr. Phosphorus Comp., pp. 145–163 (1980).
"Insoluble Compounds in Ammonium Polyphosphate Made from Wet-Process Phosphoric Acid", J. Agr. Food Chem., 16, 1968, pp. 691–697.

*Primary Examiner*—Edward J. Meros
*Attorney, Agent, or Firm*—Richard G. Miller

[57] ABSTRACT

Novel class of crystalline microporous ferroaluminophosphate compositions containing as lattice constituents in addition to $AlO_2$ and $PO_2$ structural units, ferric and/or ferrous iron in tetrahedral coordination with oxygen atoms. These compositions are prepared hydrothermally using organic templating agents and are suitably employed as catalysts or adsorbents.

19 Claims, 3 Drawing Figures

CRYSTALLINE FERROALUMINOPHOSPHATES

BACKGROUND OF THE INVENTION

1. Field of the Invention

The present invention relates to a novel class of crystalline microporous ferroaluminophosphates, to the method for their preparation, and to their use as adsorbents and catalysts. These compositions are prepared hydrothermally from gels containing reactive phosphorus, iron and aluminum compounds and organic templating agents which function in part to determine the course of the crystallization mechanism and hence the structure of the crystalline product.

2. Description of the Prior Art

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$-tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6A or less are reported in U.S. Pat. No. 3,941,871 issued Mar. 2, 1976 to Dwyer et al. Also a pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

The most recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, now U.S. Pat. No. 4,440,871, there is described a novel class of silicon-substituted aluminophosphates which are both microporous and crystalline. The materials have a three-dimensional crystal framework of $PO_2^+$, $AlO_2^-$ and $SiO_2$ tetrahedral units and, exclusive of any alkali metal or calcium which may optionally be present, an as-synthesized empirical chemical composition or an anhydrous basis of:

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved: "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

A number of compositions containing compounds of iron, aluminum and phosphorus are known and used as cements, glasses, coatings and refractories. Such compounds have also been investigated in the field of soil science, and may occur as products in procedures for removing phosphates from waste water. Crystalline iron phosphates having the crystal structure of quartz and tridymite are well known in the art, as are other dense iron phosphates and iron phosphate hydroxides such as wyllieite [a sodium aluminum iron phosphate disclosed in Mineral. Rec., 4, 131 (1973)] and ernstite [a manganese iron aluminum phosphate, Neues Jahrg. Mineral., No. 7, 289 (1970)].

A new class of metal aluminophosphates which are both crystalline and microporous and in which the metal is at least one of cobalt, zinc, magnesium or manganese is described in copending and commonly assigned application Ser. No. 514,334 filed July 5, 1983. The crystal structure of certain species of this invention are topologically related to certain species of the aforesaid copending application.

SUMMARY OF THE INVENTION

There has now been discovered a novel class of framework-substituted crystalline microporous aluminophosphates in which the substituent metal is iron, and which exhibit adsorption, ion-exchange and/or catalytic properties similar to the prior known aluminosilicate, aluminophosphate and silicoaluminophosphate molecular sieve compositions. Members of this novel class of ferroaluminophosphates have a three-dimensional microporous crystal framework structure of $AlO_2$, $FeO_2$ and $PO_2$ tetrahedral units and have an essential empirical chemical composition, on an anhydrous basis, of:

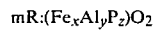

wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved, "x", "y", and "z" represent the mole fractions of iron, aluminum and phosphorus, respectively, present as tetrahedral oxides, said mole fractions being such that they are within the tetragonal compositional area defined by points A, B, C and D of the ternary diagram which is FIG. 1 of the drawings. The said points A, B, C and D representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized in accordance with the novel process of the present invention, the minimum value of "m" in the formula above is 0.02. In a preferred sub-class of the ferroaluminophosphates of this invention, the values of "x", "y" and "z" in the formula above are confined to those within the tetragonal compositional area defined by the points a, b, c and d of the ternary diagram which is FIG. 2 of the drawings, the said points a, b, c and d representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units of the present compositions can be in either the ferric or ferrous valence state, depending largely upon the source of the iron in the synthesis gel. Thus an $FeO_2$ tetrahedron in the structure can have a net charge of either $-1$ or $-2$. While it is believed that the Fe, Al and P framework constituents are present in tetrahedral coordination with oxygen (and are referred to herein as such) it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in some as yet undetermined form, and may or may not be structurally significant.

The ferroaluminophosphates of this new class of compositions exhibit molecular sieving properties, and, in common with zeolitic aluminosilicates, are capable of reversibly adsorbing water and other molecular species. Many are capable of reversibly undergoing complete dehydration without loss or change in crystal structure.

For convenience in describing the compositions of the present invention in this specification, the "shorthand" acronym "FAPO" is sometimes employed hereinafter. To identify the various structural species which make up the generic class FAPO, each species is assigned a number and is identified, for example, as FAPO-5, FAPO-11, FAPO-34 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $FeO_2^-$ and/or $AlO_2^-$ tetrahedra, $FeO_2^{-2}$ tetrahedra associated with $PO_2^+$ tetrahedra or not associated with $PO_2^+$ tetrahedra or an organic ion derived from the organic templating agent.

The aforesaid novel ferroaluminophosphates are synthesized by hydrothermal crystallization from a reaction mixture containing reactive sources of iron oxide, alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature of at least 100° C., and preferably between 100° C. and 250° C. until crystals of the metal aluminophosphate product are obtained, usually a period of from 2 hours to 2 weeks. The product is recovered by any convenient method such as centrifugation or filtration.

DETAILED DESCRIPTION OF THE INVENTION

Figure 3:
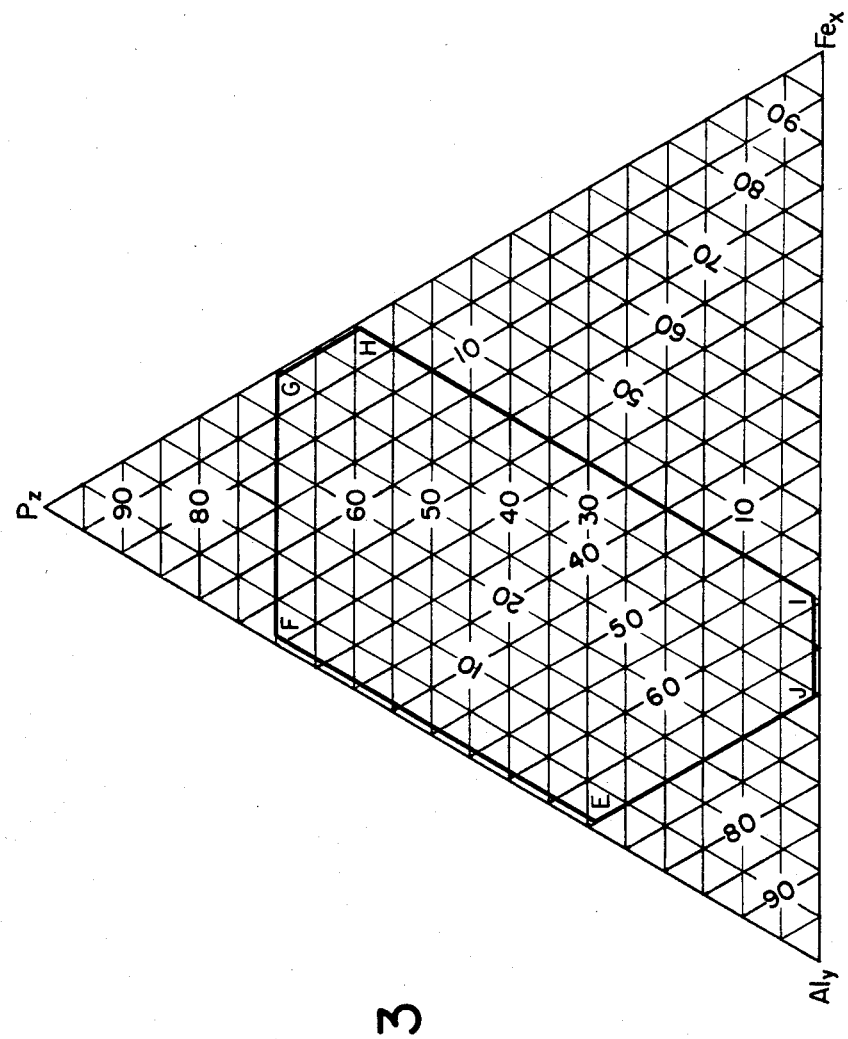

In synthesizing the FAPO compositions of the present invention, it is preferred to employ a reaction mixture composition expressed in terms of molar ratios as follows:

$$aR:(Fe_xAl_yP_z)O_2:bH_2O$$

wherein "R" is an organic templating agent; "a" has a value great enough to constitute an effective concentration of "R" and is within the range of 0 to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value of at least 0.01, and being within the hexagonal compositional areas defined by points E,F,G,H,I, and J which is shown in FIG. 3 of the drawings, the said points E,F,G,H,I, and J representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(Fe+Al+P)=(x+y+z)=1.00$ mole, whereas in many of the working examples appearing hereinafter the reaction mixtures are expressed in terms of molar oxide ratios normalized to 1.00 mole of $P_2O_5$. This latter form is readily converted to the former form by routine calculations.

In forming the reaction mixture from which the present ferroaluminophosphates are crystallized, the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and tri-amines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; trinpropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo(2,2,2,)octane; N-methyldiethanolamine, N-methylethanolamine; N-methylpiperidine; 3-methylpiperidine; N-methylcyclohexylamine; 3-methylpyridine; 4-methylpyridine; quinculidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. As will be readily apparent from the illustrative Examples set forth hereinafter, not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The most suitable phosphorus source yet found for the present process is phosphoric acid, but organic phosphates such as triethylphosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently, serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudo-boehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reactive ferrous or ferric ions. Advantageously iron salts, oxides or hydroxides are employed such as iron sulfate, iron acetate, iron nitrate, or the like. Other sources such as a freshly precipitated iron oxide, $\gamma$-FeOOH, are also suitable.

While not essential to the synthesis of FAPO compositions, it has been found that in general, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization, the FAPO product is isolated and advantageously washed with water and dried in air. The as-synthesized FAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular FAPO species. As a general rule the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the FAPO phase wherein the organic moiety occupying the intracrystalline pore system as a result of the hydrothermal crystallization process has been reduced by post-synthesis treatment such that the value of "m" in the composition formula $$mR:(Fe_xAl_yP_z)O_2$$

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized FAPO material.

Since the present FAPO compositions are formed from $AlO_2^-$, $PO_2^+$, $FeO_2^-$ and/or $FeO_2^{-2}$ units the matter of cation exchangeability is considerably more complicated than in the case of zeolitic molecular sieves in which, ideally, there is a stoichiometric relationship between $AlO_2$ tetrahedra and charge-balancing cations. In the FAPO compositions, an $AlO_2^-$ tetrahedron can be balanced electrically either by association with a $PO_2^+$ tetrahedron or a simple cation such as an alkali metal cation, a $Fe^{+2}$ or $Fe^{+3}$ cation present in the reaction mixture, or an organic cation derived from the templating agent. Similarly an $FeO_2^-$ or $FeO_2^{-2}$ tetrahedron can be balanced electrically by association with a $PO_2^+$ tetrahedron, a $Fe^{+2}$ or $Fe^{+3}$ cation, organic cation derived from the templating agent, or other metal cation introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)].

In any event, all of the FAPO compositions of the present invention examined to date have exhibited cation-exchange capacity, in some cases to a significant degree, when analyzed using ion-exchange techniques heretofore employed with zeolitic aluminosilicates. All have uniform pore diameters which are inherent in the lattice structure of each species and which are at least about 3A in diameter. Ion exchange is ordinarily possible only after the organic moiety present as a result of synthesis has been removed from the pore system. Dehydration to remove water present in the as-synthesized FAPO compositions can usually be accomplished, to some degree at least, in the usual manner without removal of the organic moiety, but the absence of the organic species greatly facilitates adsorption and desorption procedures. As illustrated hereinafter, the FAPO materials have various degrees of hydrothermal and thermal stability, some being quite remarkable in this regard, and function well as molecular sieve adsorbents and hydrocarbon conversion catalysts or catalyst bases.

The invention is illustrated by the following Examples. In each preparation of a FAPO composition, a reaction gel was prepared by combining sources of iron, aluminum, and phosphorus with water, and the gel then crystallized over a period of several hours in a sealed stainless steel reactor line with the inert plastic, polytetrafluoroethylene. Four methods were employed in mixing the reagents to form the reaction mixtures. These methods were:

(a) The iron-containing reagent was dissolved or dispersed in a solution prepared by admixing water with an 85 wt.-% aqueous solution of ortho-phosphoric acid. The resulting iron and phosphorus-containing slurry or solution was then combined with the aluminum source, and thereafter the organic templating agent (R) is added to form the final reaction mixture;

(b) The aluminum-containing reagent was added to a solution prepared by admixing water with an 85 wt.-% aqueous ortho-phosphoric acid solution. The iron source was then added, and finally the organic templating agent was incorporated to form the final reaction mixture;

(c) All reagents except the aluminum source were admixed with slight heating and then added to the aluminum source with stirring; and (d) The iron source was dissolved in water and then added to the aluminum source. Thereafter the phosphorus source was added with stirring followed by the addition of the organic templating agent, also with stirring.

In these examples in which a hydrated aluminum oxide is specified, the material employed was a commercially available pseudo-boehmite phase containing 74.2 wt. % $Al_2O_3$ and 25.8 wt. % water.

Where reaction products were subjected to X-ray analysis, the X-ray patterns were obtained using standard X-ray powder diffraction techniques. The radiation source was a high-intensity, copper target, X-ray tube operated at 50 Kv and 40 ma. The diffraction pattern from the copper $K\alpha$ radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, ms, m, w and vw which represent very strong, strong, medium strong, medium, weak and very weak respectively.

In certain instances hereinafter in the illustrative examples, the purity of a synthesized product is assessed with reference to its X-ray powder diffraction pattern. Thus, for example, if a sample of FAPO-5 is stated to be "pure FAPO-5", it is intended only that the X-ray pattern of the sample is free of lines attributable to crystalline impurities, not that there are no amorphous materials present.

EXAMPLE 1

(Preparation of FAPO-5)

(a) Using mixing Method (a), a reaction mixture was prepared having a composition, expressed in terms of molar oxide ratios, of:

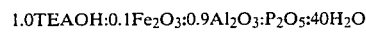

$1.0TEAOH:0.1Fe_2O_3:0.9Al_2O_3:P_2O_5:40H_2O$

The reagents employed and the quantity of each were: 0.9 grams α-iron oxyhydroxide [αFe(III)OOH]; 6.2 grams hydrated aluminum oxide; 11.5 grams of aqueous 85% ortho-phosphoric acid; 18.9 grams water; 18.4 grams of a 40% aqueous solution of tetraethylammonium hydroxide (TEAOH). The gel was crystallized at 200° C. for 24 hours. The solid product was subjected to X-ray and chemical analysis and found to comprise a major portion of the species FAPO-5 and a trace amount of another species, FAPO-18. The chemical composition of the solid product in terms of moles of tetraethylammonium hydroxide per average $TO_2$ unit was found to be:

$0.05TEAOH:(Fe_{0.07}Al_{0.47}P_{0.46})O_2:0.05H_2O$

The X-ray powder diffraction pattern was characterized by the following data:

TABLE A

| 2θ | d, (A) | 100 × I/I$_o$ |
|---|---|---|
| 7.6 | 11.63 | 100 |
| 9.7* | 9.12 | 4 |
| 13.1 | 6.76 | 10 |
| 15.1 | 5.87 | 25 |
| 15.7* | 5.64 | 1 (sh) |
| 17.1* | 5.19 | 4 |
| 18.0* | 4.93 | 1 |
| 20.0 | 4.44 | 53 |
| 21.2 | 4.19 | 60 |
| 22.6 | 3.93 | 79 |
| 25.0 | 3.562 | 3 |

TABLE A-continued

| 2θ | d, (A) | 100 × I/I$_o$ |
|---|---|---|
| 26.2 | 3.401 | 24 |
| 28.4 | 3.143 | 2 |
| 29.3 | 3.048 | 14 |
| 30.4 | 2.940 | 14 |
| 31.5* | 2.840 | 1 |
| 32.5* | 2.755 | 1 |
| 33.4* | 2.683 | 3 |
| 34.0 | 2.637 | 4 |
| 34.9 | 2.571 | 12 |
| 36.8 | 2.442 | 6 |
| 37.3 | 2.411 | 3 (sh) |
| 38.0 | 2.368 | 10 |
| 40.1 | 2.249 | 1 |
| 41.3* | 2.186 | 2 |
| 41.8 | 2.161 | 1 |
| 42.6 | 2.122 | 2 |
| 43.0 | 2.103 | 1 |
| 44.0 | 2.058 | 1 |
| 48.2 | 1.888 | 2 |
| 53.3 | 1.719 | 2 |

\* = line possibly attributable to an impurity
(sh) = shoulder (b) The FAPO-5 composition of part (a) of this Example was calcined in air at 600° C. for 3 hours. The X-ray powder diffraction pattern of he calcined product was characterized by the following data:

TABLE B

| 2θ | d, (A) | 100 × I/I$_o$ |
|---|---|---|
| 7.4 | 11.95 | 100 |
| 9.6* | 9.21 | 8 |
| 12.9 | 6.86 | 18 |
| 13.4* | 6.61 | 1 (sh) |
| 14.9 | 5.95 | 6 |
| 17.2* | 5.16 | 1 |
| 19.8 | 4.48 | 22 |
| 21.2 | 4.19 | 38 |
| 22.5 | 3.95 | 65 |
| 24.2* | 3.68 | 3 |
| 24.9 | 3.58 | 3 |
| 26.0 | 3.427 | 21 |
| 29.1 | 3.069 | 12 |
| 30.1 | 2.969 | 10 |
| 33.1* | 2.706 | 10 |
| 33.8 | 2.652 | 4 (sh) |
| 34.6* | 2.592 | 8 |
| 35.7* | 2.515 | 10 |
| 37.1 | 2.423 | 3 |
| 37.9 | 2.374 | 7 |
| 39.4* | 2.287 | 1 |
| 40.8* | 2.212 | 4 |
| 41.7* | 2.166 | 1 |
| 42.4 | 2.132 | 1 |
| 43.1 | 2.099 | 1 |
| 43.8 | 2.067 | 1 |
| 47.8 | 1.903 | 2 |
| 49.4* | 1.845 | 3 |
| 54.0 | 1.698 | 4 |

\* = line possibly attributable to an impurity
(sh) = shoulder (c) Energy dispersive analysis by X-ray (EDAX) in conjunction with scanning electron microscope studies on a particle of the solid product of part (a) having a minimal amount of debris associated therewith had a Fe:P:Al peak height ratio of 0.04:1.0:0.98.

EXAMPLE 2

(Preparation of FAPO-5)

(a) Using mixing Method (b), a reaction gel was prepared having a composition expressed in terms of molar oxide ratios of:

1.0TPAOH:0.2Fe$_2$O$_3$:0.8Al$_2$O$_3$:P$_2$O$_5$:50H$_2$O

The reaction employed and the quantity of each were: 3.6 grams γ-iron oxyhydroxide [γFe(III)OOH]; 11.0 grams of hydrated aluminum oxide; 23.1 grams of 85% aqueous ortho-phosphoric acid; 16.9 grams of water; and 81.4 grams of a 25% aqueous solution of tetrapropylammonium hydroxide (TPAOH). The gel was crystallized for 24 hours at 150° C. The solid product was identified by X-ray analysis to be principally FAPO-5 with a minor proportion of an unidentified crystalline composition and a crystalline material having the structure of variscite.

(b) The procedure of part (a) above was repeated and produced the same products.

EXAMPLE 3

(Preparation of FAPO-5)

(a) Using mixing Method (a), the following reagents were admixed to form a reaction mixture: 4.0 grams of iron (II) chloride tetrahydrate [FeCl$_2$.4H$_2$O]; 12.4 grams of hydrated aluminum oxide; 23.1 grams of an 85% aqueous ortho-phosphoric acid solution; 36.5 grams of water; and 36.8 grams of a 40% aqueous tetraethylammonium hydroxide solution. The composition of the final reaction mixture, in terms of molar oxide ratios was:

1.0TEAOH:0.1Fe$_2$O$_3$:0.9Al$_2$O$_3$:P$_2$O$_5$:40H$_2$O

The gel was crystallized for 24 hours at 150° C. The resulting solid product was found to have the following X-ray powder diffraction pattern which is characteristic of FAPO-5.

TABLE C

| 2θ | d, (A) | 100 × I/I$_o$ |
|---|---|---|
| 7.4 | 11.95 | 91 |
| 12.8 | 6.92 | 10 |
| 14.8 | 5.99 | 26 |
| 19.7 | 4.51 | 70 |
| 21.0 | 4.23 | 66 |
| 22.4 | 3.97 | 100 |
| 24.8 | 3.59 | 5 |
| 25.9 | 3.440 | 34 |
| 29.0 | 3.079 | 18 |
| 30.1 | 2.969 | 20 |
| 33.6 | 2.667 | 5 |
| 34.5 | 2.600 | 17 |
| 36.9 | 2.436 | 5 |
| 37.7 | 2.386 | 14 |
| 41.5 | 2.176 | 2 |
| 42.2 | 2.141 | 4 |
| 42.7 | 2.118 | 2 |
| 43.6 | 1.076 | 2 |
| 47.7 | 1.907 | 6 |
| 55.7 | 1.650 | 5 |

(b) A reaction mixture having the same composition as in part (a) above was prepared using the same reagents and using the same mixing Method (a). The gel was crystallized for 144 hours at 150° C. and the solid product subjected to X-ray and chemical analysis. The chemical composition of the product in terms of moles of tetraethylammonium hydroxide per average TO$_2$ unit was:

0.05TEAOH:(Fe$_{0.04}$Al$_{0.47}$P$_{0.49}$)O$_2$:0.04H$_2$O

The X-ray powder diffraction pattern of the as-synthesized product was characterized by the following data:

TABLE D

| 2θ | d, (A) | 100 × I/I₀ |
|---|---|---|
| 7.4 | 11.95 | 100 |
| 12.9 | 6.86 | 12 |
| 15.0 | 5.91 | 23 |
| 19.8 | 4.48 | 65 |
| 21.1 | 4.19 | 68 |
| 22.5 | 3.95 | 98 |
| 24.8 | 3.59 | 4 |
| 26.0 | 3.427 | 33 |
| 27.2* | 3.278 | 3 |
| 29.0 | 3.079 | 18 |
| 30.1 | 2.969 | 18 |
| 33.7 | 2.660 | 5 |
| 34.6 | 2.592 | 17 |
| 37.1 | 2.423 | 4 |
| 37.8 | 2.380 | 11 |
| 41.0 | 2.201 | 1 |
| 41.8 | 2.161 | 2 |
| 42.4 | 2.103 | 2 |
| 43.0 | 2.132 | 3 |
| 43.8 | 2.067 | 1 |
| 45.2 | 2.008 | 1 |
| 45.8 | 1.981 | 1 |
| 47.8 | 1.903 | 5 |
| 51.8 | 1.765 | 2 |
| 52.2 | 1.752 | 2 |

* = line possible attributable to an impurity (c) The as-synthesized FAPO-5 composition part (b) was calcined in air at 600° C. for 3 hours, and then subjected to X-ray analysis. The X-ray powder pattern obtained was characterized by the following data:

TABLE E

| 2θ | d, (A) | 100 × I/I₀ |
|---|---|---|
| 7.3 | 12.11 | 100 |
| 12.8 | 6.92 | 13 |
| 14.8 | 5.99 | 5 |
| 19.6 | 4.53 | 24 |
| 21.1 | 4.21 | 31 |
| 22.3 | 3.99 | 46 |
| 24.7 | 3.60 | 1 |
| 25.8 | 3.453 | 16 |
| 28.9 | 3.089 | 8 |
| 29.9 | 2.988 | 8 |
| 33.6 | 2.667 | 3 |
| 34.4 | 2.607 | 7 |
| 36.9 | 2.436 | 2 |
| 37.8 | 2.380 | 5 |
| 40.7 | 2.217 | <1 |
| 41.3 | 2.186 | 1 |
| 42.2 | 2.141 | 2 |
| 43.0 | 2.103 | 1 |
| 43.6 | 2.076 | 1 |
| 44.8 | 2.023 | <1 |
| 45.4 | 1.998 | <1 |
| 47.4 | 1.918 | 3 |
| 51.2 | 1.784 | 1 |
| 52.0 | 1.759 | 1 |
| 55.2 | 1.664 | 1 |

(d) Adsorption capacities were measured on the calcined FAPO-5 part (c) supra using standard McBain-Bakr gravimetric adsorption apparatus. The following data were obtained on a sample activated at 350° C.

| Adsorbate | Kinetic Diameter, A | Pressure Torr | Temp., °C. | Wt. % Absorbed |
|---|---|---|---|---|
| O₂ | 3.46 | 98 | −183 | 14.3 |
| O₂ | 3.46 | 758 | −183 | 19.4 |
| Neopentane | 6.2 | 100 | 25.8 | 5.8 |
| H₂O | 2.65 | 4.6 | 22.4 | 19.4 |
| H₂O | 2.65 | 19.4 | 23.8 | 28.3 |

(e) The procedure of part (b) above was repeated to form a gel having the same chemical composition as in part (b). This gel was crystallized at 200° C. for 332 hours. The white portion of the product solids was subjected to chemical and X-ray analysis and found to be principally FAPO-5 with a minor portion of FAPO-34 and a trace amount of FAPO-20. The chemical composition of the white solids was:

0.07TEAOH:(Fe$_{0.07}$Al$_{0.43}$P$_{0.50}$)O$_2$:0.26H$_2$O (f) Particles in the 20–40 micrometer range taken from the FAPO-5 product of part (b) of this Example were analyzed by EDAX and found to have a Fe:P:Al peak height ratio of 0.06:1.0:0.96.

EXAMPLE 4

(Preparation of FAPO-5)

(a) Using iron (II) acetate as the source of iron, FAPO-5 was produced from a reaction mixture prepared using mixing Method (a) and the following proportions of reagents: 3.5 grams of anhydrous iron (II) acetate [Fe(II)(OAc)₂]; 12.4 grams of a hydrated aluminum oxide; 23.1 grams of an 85% aqueous solution of ortho-phosphoric acid; 37.9 grams of water; and 36.8 grams of a 40% aqueous solution of tetraethylammonium hydroxide. The reaction mixture had the following chemical composition, expressed in terms of molar oxide ratios:

1.0TEAOH:0.1Fe$_2$O$_3$:0.9Al$_2$O$_3$:P$_2$O$_5$:40 H$_2$O

A portion of the gel was crystallized for 40 hours at 200° C., and the solid product found, by X-ray analysis, to contain a major proportion of FAPO-5, a minor proportion of FAPO-34 and a trace amount of FAPO-20. The chemical composition of a portion of the solid product was found by chemical analysis to be:

0.07TEAOH:(Fe$_{0.08}$Al$_{0.47}$P$_{0.45}$)O$_2$:0.30H$_2$O (b) The remaining portion of the gel of part (a) above, was crystallized at 150° C. for 168 hours and found to produce essentially the same solid product as in part (a) except that no FAPO-20 was detected.

Figure 1:
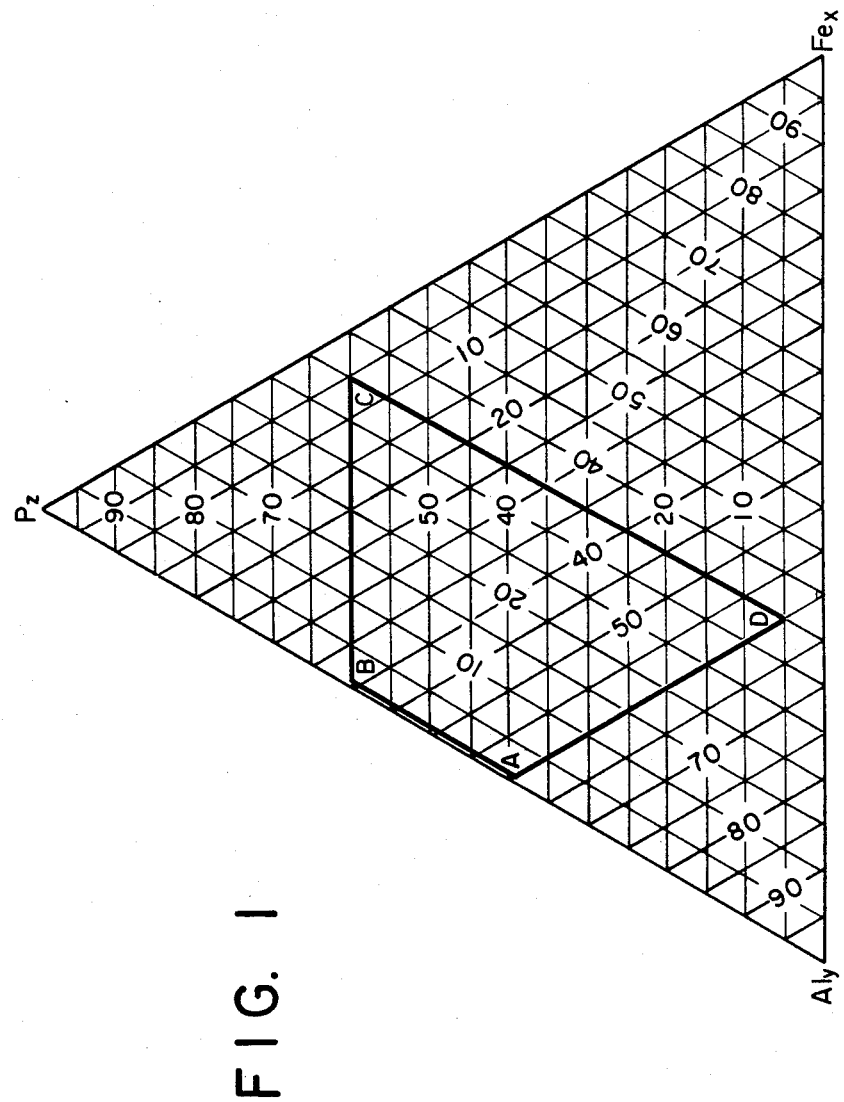
Figure 2:
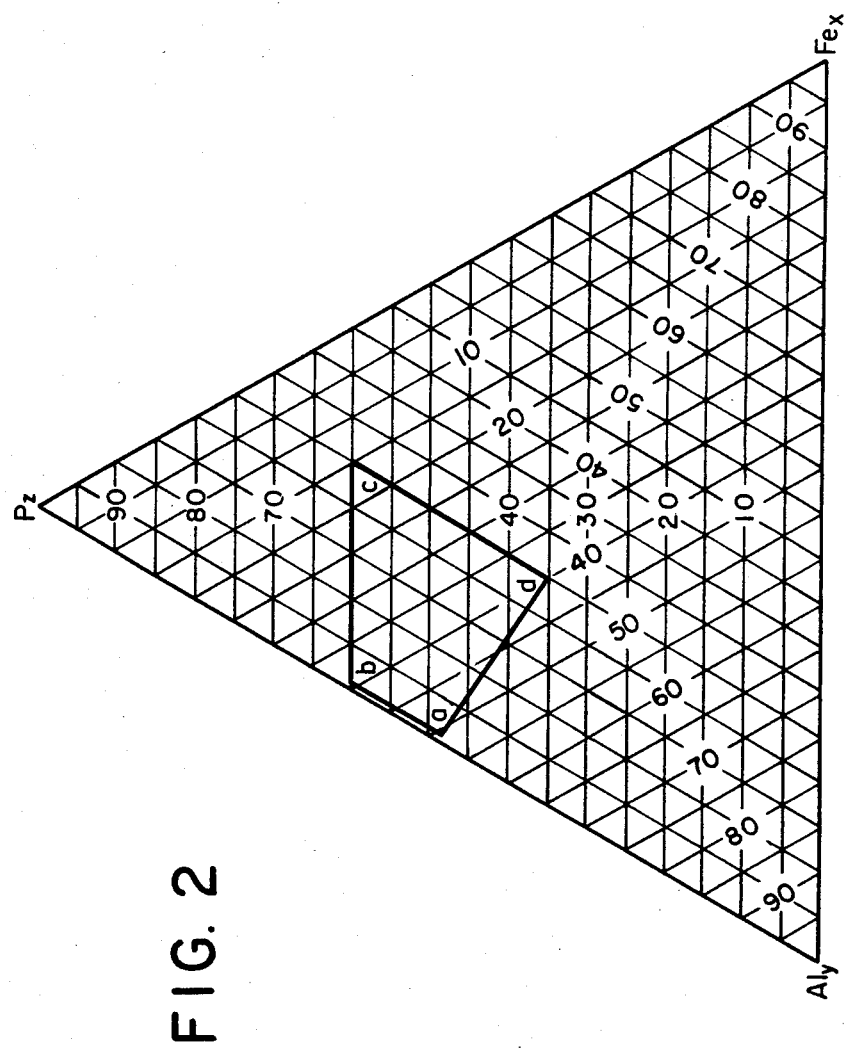

The species FAPO-5 as referred to herein is a ferroaluminophosphate material having a three-dimensional microporous crystal framework structure of the tetrahedral units PO$_2^+$, AlO$_2^-$ and at least one of FeO$_2^-$ and FeO$_2^{-2}$, and whose essential empirical chemical composition on an anhydrous basis is:

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, "x", "y" and "z" represent respectively, the mole fractions of iron, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said ferroaluminophosphate having a characteristic X-ray powder diffraction pattern which contains at least the d-spacings set forth below in Table I. In the form as synthesized in accordance with the process of this invention, "m" has a value of from 0.02 to 0.3.

TABLE I

| 2θ | d, (A) | Relative Intensity |
|---|---|---|
| 7.3–7.6 | 12.1–11.6 | vs |
| 14.8–15.1 | 5.99–5.87 | w–m |
| 19.6–20.0 | 4.53–4.44 | m–s |
| 21.0–21.2 | 4.23–4.19 | m–s |
| 22.3–22.6 | 3.99–3.93 | s–vs |
| 25.8–26.2 | 3.453–3.401 | m |

All of the as-synthesized FAPO-5 compositions for which X-ray powder diffraction data have presently been obtained have patterns which are within the generalized pattern of Table II below:

TABLE II

| 2θ | d, (A) | 100 × I/I$_o$ |
|---|---|---|
| 7.3–7.6 | 12.1–11.63 | 91–100 |
| 12.8–13.1 | 6.92–6.76 | 10–18 |
| 14.8–15.1 | 5.99–5.87 | 5–26 |
| 19.6–20.0 | 4.53–4.44 | 22–70 |
| 21.0–21.2 | 4.23–4.19 | 31–68 |
| 22.3–22.6 | 3.99–3.93 | 46–100 |
| 24.2–25.0 | 3.68–3.56 | 1–5 |
| 25.8–26.2 | 3.453–3.401 | 16–34 |
| 28.9–29.3 | 3.089–3.048 | 12–18 |
| 29.9–30.4 | 2.998–2.940 | 8–20 |
| 33.6–34.0 | 2.667–2.637 | 3–5 |
| 34.4–34.9 | 2.607–2.571 | 7–17 |
| 36.9–37.3 | 2.436–2.411 | 2–5 |
| 37.7–38.0 | 3.386–2.368 | 5–14 |
| 40.7–41.0 | 2.217–2.201 | 0–4 |
| 41.3–41.8 | 2.186–2.161 | 1–2 |
| 42.2–42.6 | 2.141–2.122 | 1–4 |
| 42.7–43.1 | 2.118–2.099 | 0–2 |
| 43.6–44.0 | 2.076–2.058 | 1–2 |
| 44.8–45.2 | 2.003–2.000 | 0–1 |
| 45.4–45.8 | 1.998–1.981 | 0–1 |
| 47.4–48.2 | 1.918–1.888 | 2–6 |
| 51.2 | 1.784 | 0–1 |
| 51.8–52.0 | 1.765–1.759 | 0–2 |
| 52.2 | 1.752 | 0–2 |
| 54.0 | 1.698 | 0–4 |
| 55.2 | 1.664 | 0–1 |
| 55.7 | 1.650 | 0–5 |

EXAMPLE 5

(Preparation of FAPO-11)

(a) Using mixing Method (a), a reaction mixture was prepared having a composition, expressed in terms of molar oxide ratios, of:

1.0Pr$_2$NH:0.1Fe$_2$O$_3$:0.9Al$_2$O$_3$:P$_2$O$_5$:43H$_2$O

The reagents and the amounts thereof utilized in forming the reaction mixture were: 7.0 grams of anhydrous iron (II) acetate [Fe(II)(OAc)$_2$]; 24.7 grams of a hydrated aluminum oxide; 46.1 grams of an 85% aqueous ortho-phosphoric acid solution; 120 grams of water and 20.2 grams of di-n-propylamine. A portion of the resulting gel was crystallized at 200° C. for 24 hours. The recovered solid product was subjected to X-ray and chemical analysis and found to comprise FAPO-11 as the principal constituent along with a trace amount of FAPO-31. The chemical composition of the solid product, in terms of moles of Pr$_2$NH per average TO$_2$ unit, was

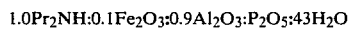
0.04Pr$_2$NH:(Fe$_{0.10}$Al$_{0.43}$P$_{0.47}$)O$_2$:0.09H$_2$O

The X-ray powder diffraction pattern of the solid product was characterized by the following data:

TABLE F

| 2θ | d, (A) | 100 × I/I$_o$ |
|---|---|---|
| 8.1 | 10.92 | 34 |
| 8.5* | 10.40 | 33 (sh) |
| 9.5 | 9.31 | 44 |
| 13.2 | 6.71 | 12 |
| 13.7* | 6.46 | 4 |
| 15.7 | 5.64 | 23 |
| 16.2 | 5.47 | 2 |
| 18.3* | 4.85 | 7 |
| 19.0 | 4.67 | 4 |
| 20.3 | 4.37 | 52 |
| 21.1 | 4.21 | 92 |
| 22.2 | 4.00 | 67 (sh) |
| 22.6 | 3.93 | 100 |
| 23.2 | 3.83 | 64 (sh) |
| 24.8 | 3.59 | 6 |
| 24.8* | 3.453 | 5 |
| 26.4 | 3.376 | 16 |
| 27.0 | 3.302 | 6 |
| 28.0* | 3.187 | 10 |
| 28.7 | 3.110 | 12 |
| 29.1 | 3.069 | 3 |
| 29.6 | 3.018 | 6 |
| 31.6 | 2.831 | 16 |
| 32.9 | 2.722 | 12 |
| 34.2 | 2.622 | 6 |
| 35.1* | 2.557 | 3 |
| 36.5 | 2.462 | 2 |
| 37.8 | 2.380 | 11 |
| 39.4 | 2.287 | 4 |
| 42.9 | 2.108 | 2 |
| 44.8 | 2.023 | 6 |
| 46.6 | 1.949 | 1 |
| 48.6 | 1.873 | 2 |
| 50.5 | 1.807 | 2 |
| 51.4* | 1.778 | 2 |
| 54.6 | 1.681 | 2 |
| 55.3 | 1.661 | 2 |

* = line possibly attributable to an impurity
(sh) = shoulder (b) Particles of the solid FAPO-11 product of part (c) in the size range of 5–35 micrometers were analyzed by EDAX (energy dispersive analysis by X-ray) and found to have a Fe:P:Al peak height ratio of 0.07:1.0:0.87.

(c) The remaining portion of the gel from part (a) above was crystallized at 150° C. for 48 hours. The crystalline product exhibited essentially the same X-ray powder diffraction pattern as the product of part (a) and was thus established to be FAPO-11.

(d) The solid product of part (c) was calcined in air at 550° C. for 7 hours. The X-ray powder diffraction pattern of the calcined product was characterized by the following data:

TABLE G

| 2θ | d, (A) | 100 × I/I$_o$ |
|---|---|---|
| 8.2 | 10.78 | 31 (sh) |
| 8.5* | 10.40 | 54 |
| 9.7 | 9.12 | 44 |
| 12.8* | 6.92 | 17 |
| 13.5 | 6.56 | 15 |
| 14.8* | 6.99 | 4 |
| 16.1 | 5.50 | 39 |
| 17.0* | 5.22 | 4 |
| 18.4* | 4.82 | 4 |
| 19.5 | 4.55 | 15 (sh) |
| 20.0* | 4.44 | 29 (sh) |
| 20.3 | 4.37 | 53 |
| 21.6 | 4.11 | 22 (sh) |
| 21.9 | 4.06 | 93 |
| 22.5 | 3.95 | 100 |
| 23.4 | 3.80 | 55 |
| 24.0* | 3.71 | 1 |
| 24.3* | 3.66 | 1 |

TABLE G-continued

| 2θ | d, (A) | 100 × I/I$_o$ |
|---|---|---|
| 25.2 | 3.534 | 7 |
| 25.7* | 3.466 | 17 |
| 26.5 | 3.363 | 9 |
| 27.2* | 3.278 | 16 |
| 27.8* | 3.209 | 16 |
| 29.6 | 3.018 | 22 |
| 30.3* | 2.950 | 9 |
| 31.7 | 2.823 | 22 |
| 32.5 | 2.755 | 14 |
| 33.9* | 2.644 | 3 |
| 34.4 | 2.607 | 1 |
| 35.1* | 2.557 | 8 |
| 35.5 | 2.529 | 8 |
| 37.2* | 2.417 | 8 |
| 38.2 | 2.356 | 8 |
| 38.6* | 2.332 | 8 |
| 39.3 | 2.292 | 1 |
| 43.7* | 2.071 | 1 |
| 45.0 | 2.014 | 1 |
| 49.1 | 1.855 | 2 |

\* = lines possibly attributable to an impurity
(sh) = shoulder (e) The sample used in part (d) supra was calcined in air at 500° C. for 5 hours and then at 600° C. for 2½ hours. Adsorption capacities were then measured. The data obtained is as follows:

| Adsorbate | Kinetic Diameter, A | Pressure Torr | Temp., °C. | Wt. % Adsorbed |
|---|---|---|---|---|
| O$_2$ | 3.46 | 100 | −183 | 8.2 |
| O$_2$ | 3.46 | 750 | −183 | 11.7 |
| n-Hexane | 4.3 | 97 | 23.5 | 5.9 |
| i-Butane | 5.0 | 740 | 24.6 | 3.9 |
| Neopentane | 6.2 | 101 | 24.1 | 1.2 |
| H$_2$O | 2.65 | 4.6 | 24.4 | 14.2 |
| H$_2$O | 2.65 | 19.9 | 24.5 | 24.2 |

The species FAPO-11 as referred to herein is a ferroaluminophosphate material having a three-dimensional microporous crystal framework structure of the tetrahedral units PO$_2^+$, AlO$_2^-$ and at least one of FeO$_2^-$ and FeO$_2^{-2}$ and whose essential empirical chemical composition on an anhydrous basis is:

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, "x", "y" and "z" represent respectively, the mole fractions of iron, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said ferroaluminophosphate havimg a characteristic X-ray powder diffraction pattern which contains at least the d-spacings set forth between in Table III. In the form as synthesized in accordance with the process of this invention, "m" has a value of from 0.02 to 0.3.

TABLE III

| 2θ | d (A) | Relative Intensity |
|---|---|---|
| 8.1–8.2 | 10.92–10.78 | m |
| 9.5–9.7 | 9.31–9.12 | m |
| 20.3 | 4.37 | m |

TABLE III-continued

| 2θ | d (A) | Relative Intensity |
|---|---|---|
| 21.1–21.6 | 4.21–4.11 | m–vs |
| 21.9–22.2 | 4.06–4.00 | s–vs |
| 22.5–22.6 | 3.95–3.93 | vs |
| 23.2–23.4 | 3.83–3.80 | m–s |

All of the as-synthesized FAPO-11 compositions for which X-ray powder diffraction data have presently been obtained have patterns which are within the generalized pattern of Table IV below.

TABLE IV

| 2θ | d, (A) | 100 × I/I$_o$ |
|---|---|---|
| 8.1–8.2 | 10.92–10.78 | 31–34 |
| 8.5 | 10.40 | (sh) |
| 9.5–9.7 | 9.31–9.12 | 44–54 |
| 13.2–13.5 | 6.71–6.56 | 12–15 |
| 15.7–16.1 | 5.64–5.50 | 23–39 |
| 16.2 | 5.47 | 0–2 |
| 19.0–19.5 | 4.67–4.55 | 4–15 |
| 20.3 | 4.37 | 52–53 |
| 21.1–21.6 | 4.21–4.11 | 22–92 |
| 21.9–22.2 | 4.06–4.00 | 67–93 |
| 22.5–22.6 | 3.95–3.93 | 100 |
| 23.2–23.4 | 3.83–3.80 | 55–64 |
| 24.8–25.2 | 3.59–3.53 | 6–7 |
| 26.4–26.5 | 3.376–3.363 | 9–16 |
| 27.0–27.2 | 3.302–3.196 | 0–6 |
| 28.7 | 3.110 | 0–12 |
| 29.1 | 3.096 | 0–3 |
| 29.6 | 3.018 | 6–22 |
| 31.6–31.7 | 2.831–2.823 | 16–22 |
| 32.5–32.9 | 2.755–2.722 | 12–14 |
| 34.2–34.4 | 2.622–2.607 | 1–6 |
| 35.5 | 2.529 | 0–8 |
| 36.5 | 2.462 | 0–2 |
| 37.8–38.2 | 2.380–2.356 | 8–11 |
| 39.3–39.4 | 2.292–2.287 | 1–4 |
| 42.9 | 2.108 | 1–2 |
| 44.8–45.0 | 2.041–2.023 | 1–6 |
| 46.6 | 1.949 | 0–1 |
| 48.6 | 1.873 | 0–2 |
| 49.1 | 1.855 | 0–2 |
| 50.5 | 1.807 | 0–2 |
| 54.6 | 1.681 | 0–2 |
| 55.3 | 1.661 | 0–2 |

EXAMPLE 6

(Preparation of FAPO-16)

(a) Using mixing Method (b), a reaction mixture was prepared from: 2.9 grams of anhydrous iron (II) acetate [Fe(II)(OAc)$_2$]; 30.6 grams of aluminum isopropoxide [Al(OC$_3$H$_7$)$_3$]; 19.2 grams of an 85% aqueous orthophosphoric acid solution; 67.7 grams of water; and 9.3 grams of quinuclidine (C$_7$H$_{13}$N). The composition of the reaction mixture, in terms of molar oxide ratios, was:

1.0C$_7$H$_{13}$N:0.1Fe$_2$O$_3$:0.9Al$_2$O$_3$:P$_2$O$_5$:50H$_2$O

A portion of the resulting gel was crystallized at 150° C. for 52 hours. The solid product as subjected to X-ray analysis and was found to be principally FAPO-16. The X-ray powder diffraction pattern of the solid product was characterized by the following data:

TABLE H

| 2θ | d, (A) | 100 × I/I$_o$ |
|---|---|---|
| 7.4* | 11.95 | 6 |
| 9.2* | 9.61 | 3 |
| 11.4 | 7.76 | 58 |

TABLE H-continued

| 2θ | d, (A) | 100 × I/I$_o$ |
|---|---|---|
| 14.8* | 5.99 | 2 |
| 16.1* | 5.50 | 1 |
| 17.4 | 5.10 | 3 |
| 18.8 | 4.72 | 52 |
| 19.8* | 4.48 | 3 |
| 20.6* | 4.31 | 3 |
| 21.1* | 3 | (sh) |
| 4.21 | | |
| 22.0 | 4.04 | 100 |
| 22.9 | 3.88 | 2 (sh) |
| 25.9* | 3.440 | 1 (sh) |
| 26.6 | 3.351 | 25 |
| 27.1* | 3.290 | 3 |
| 29.0 | 3.079 | 8 |
| 29.4* | 3.038 | 2 |
| 29.7 | 3.008 | 28 |
| 31.4* | 2.849 | 2 |
| 32.7 | 2.739 | 5 |
| 34.7 | 2.585 | 5 |
| 37.9 | 2.374 | 9 |
| 39.8 | 2.265 | 2 |
| 44.2 | 2.049 | 3 |
| 48.4 | 1.881 | 5 |
| 52.4 | 1.746 | 2 |
| 53.7* | 1.707 | 1 |
| 54.6 | 1.681 | 2 |

* = line possibly attributable to an impurity
(sh) = shoulder (b) A second portion of the reaction gel of part (a) above, was crystallized at 150° C. for 175 hours. The solid product was also established by its X-ray powder diffraction pattern to be FAPO-16, and was somewhat more pure than the product of part (a). The chemical composition of the product, in terms of moles of quinuclidine per average TO$_2$ units was:

0.12C$_7$H$_{13}$N:(Fe$_{0.04}$Al$_{0.46}$P$_{0.50}$)O$_2$:0.58H$_2$O

The X-ray powder diffraction pattern of the product was characterized by the following data:

TABLE J

| 2θ | d, (A) | 100 × I/I$_o$ |
|---|---|---|
| 9.2 | 9.61 | 1 |
| 11.5 | 7.69 | 58 |
| 13.1* | 6.76 | 2 |
| 14.8* | 5.99 | 1 |
| 17.4 | 5.10 | 3 |
| 18.8 | 4.72 | 58 |
| 20.6* | 4.31 | 2 |
| 22.0 | 4.04 | 100 |
| 23.1 | 3.85 | 5 (sh) |
| 26.6 | 3.351 | 23 |
| 29.1 | 3.069 | 8 |
| 29.8 | 2.998 | 27 |
| 32.8 | 2.730 | 4 |
| 34.8 | 2.578 | 7 |
| 35.7* | 2.515 | 2 |
| 38.0 | 2.368 | 10 |
| 39.7 | 2.270 | 2 |
| 44.4 | 2.040 | 3 |
| 48.5 | 1.877 | 8 |
| 52.4 | 1.746 | 3 |
| 54.8 | 1.675 | 3 |

* = line possibly attributable to an impurity
(sh) = shoulder (c) The as-synthesized FAPO-16 product of part (b) above was calcined in air for 2 hours at 600° C. The X-ray powder diffraction pattern of the calcined material was characterized by the following data:

TABLE K

| 2θ | d, (A) | 100 × I/I$_o$ |
|---|---|---|
| 9.2* | 9.61 | 2 |
| 11.3 | 7.83 | 100 |
| 13.1* | 6.76 | 7 |
| 18.6 | 4.77 | 21 |
| 21.9 | 4.06 | 50 |
| 22.9 | 3.88 | 12 |
| 26.5 | 3.363 | 21 |
| 29.0 | 3.079 | 6 |
| 29.7 | 3.008 | 36 |
| 32.6 | 2.747 | 8 |
| 34.6 | 2.592 | 10 |
| 37.9 | 2.374 | 6 |
| 44.2 | 2.049 | 2 |
| 48.4 | 1.881 | 4 |
| 52.2 | 1.752 | 2 |
| 54.8 | 1.675 | 2 |

* = line possibly attributable to an impurity (d) A portion of the product of part (a) above was heated under vacuum at 350° C. for 16 hours in a standard McBain-Bakr gravimetric apparatus, and thereafter the following adsorption data obtained:

| Adsorbate | Kinetic Diameter, A | Pressure Torr | Temp., °C. | Wt. % Adsorbed |
|---|---|---|---|---|
| O$_2$ | 3.46 | 100 | −183 | 2.3 |
| O$_2$ | 3.46 | 734 | −183 | 7.9 |
| H$_2$O | 2.65 | 4.6 | 24.4 | 18.2 |
| H$_2$O | 2.65 | 18.5 | 24.0 | 25.1 |

(d) A third portion of the gel of part (a) above was crystallized at 200° C. for 52 hours. By X-ray analysis, the resulting solid product was found to be principally FAPO-16 with a minor amount of an impurity phase having some similarity to FAPO-17.

(e) Using mixing Method (a), 5.8 grams of iron (II) acetate, 61.3 grams of aluminum isopropoxide, 38.4 grams of 85% aqueous ortho-phosphoric acid and 135.4 grams of water were admixed and the resulting mixture divided into two portions of equal weight. To one portion 9.3 grams of quinuclidine (C$_7$H$_{13}$N) was added to form a reaction mixture having a composition in terms of molar oxide ratios of:

1.0C$_7$H$_{13}$N:0.1Fe$_2$O$_3$:0.9Al$_2$O$_3$:P$_2$O$_5$:50H$_2$O

The reaction mixture was crystallized at 225° C. for 98 hours. By X-ray analysis the resulting solid product was found to comprise a major proportion of FAPO-16 in combination with a minor proportion of FAPO-17.

The species FAPO-16 as referred to herein is a ferroaluminophosphate material having a three-dimensional microporous crystal framework structure of the tetrahedral units PO$_2^+$, AlO$_2^-$ and at least one of FeO$_2^-$ and FeO$_2^{-2}$, and whose essential empirical chemical composition on an anhydrous basis is:

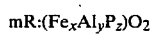

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, "x", "y" and "z" represent respectively, the mole fractions of iron, aluminum and phosphorus present in the oxide moiety, said mole fractions being within the compositional area bounded by points A, B, C and D on the ternary diagram which is FIG. 1, or preferably within the area bounded by points a, b, c, and d on the ternary diagram which is FIG. 2, said ferroaluminophosphate having a characteristic X-ray powder diffraction pattern which contains at least the d-spacings set forth below in Table V. In the form as synthesized in accordance with the process of this invention, "m" has a value of from 0.02 to 0.3.

TABLE V

| 2θ | d (A) | Relative Intensity |
|---|---|---|
| 11.3–11.5 | 7.83–7.69 | m–vs |
| 18.6–18.8 | 4.77–4.72 | m |
| 21.9–22.0 | 4.06–4.04 | m–vs |
| 26.5–26.6 | 3.363–3.351 | m |
| 29.7–29.8 | 3.008–2.998 | m |

All of the as-synthesized FAPO-16 compositions for which X-ray powder diffraction data have presently been obtained have patterns which are within the generalized pattern of Table VI below.

TABLE VI

| 2θ | d, (A) | 100 × I/I$_o$ |
|---|---|---|
| 11.3–11.5 | 7.83–7.69 | 58–100 |
| 17.4 | 5.10 | 3 |
| 18.6–18.8 | 4.77–4.72 | 21–58 |
| 21.9–22.0 | 4.06–4.04 | 50–100 |
| 22.9–23.1 | 3.88–3.85 | 2–12 (sh) |
| 26.5–26.6 | 3.440–3.363 | 21–25 |
| 29.0–29.1 | 3.079–3.069 | 6–8 |
| 29.7–29.8 | 3.008–2.998 | 28–36 |
| 32.6–32.8 | 2.747–2.730 | 4–8 |
| 34.6–34.8 | 2.592–2.578 | 5–10 |
| 37.9–38.0 | 2.374–2.368 | 6–10 |
| 39.7–39.8 | 2.270–2.265 | 2 |
| 44.2–44.4 | 2.049–2.040 | 2–3 |
| 48.4–48.5 | 1.881–1.877 | 4–8 |
| 52.2–52.4 | 1.752–1.446 | 2–3 |
| 54.6–54.8 | 1.681–1.675 | 2–3 |

EXAMPLE 7

(Preparation of FAPO-17)

(a) 8.3 grams of cyclohexylamine was added to the remaining half of the reaction mixture from Example 6(e). The resulting mixture had a composition of:

$$1.0C_6H_{11}NH_2:0.1Fe_2O_3:0.9Al_2O_3:P_2O_5:50H_2O$$

One half of this new reaction mixture was crystallized at 200° C. for 112 hours, and the other half crystallized at 200° C. for 276 hours. After 112 hours the product was found by X-ray analysis to comprise principally FAPO-5 along with some unidentified crystalline impurity. After 276 hours the product was principally FAPO-17 along with unidentified crystalline impurity. A relatively pure FAPO-17 was physically separated from the mixture.

(b) Energy dispersive analysis by X-ray (EDAX) in conjunction with scanning electron microscope studies on a particle of the relatively pure FAPO-17 product of part (a) above having a minimal amount of debris associated therewith established that the Fe:P:Al peak height ratio of the composition was 0.4:1.0:0.82. The X-ray powder diffraction pattern of the predominantly FAPO-17 product was characterized by the following data:

TABLE L

| 2θ | d, (A) | 100 × I/I$_o$ | |
|---|---|---|---|
| 7.8 | 11.33 | 100 | |
| 9.8 | 9.03 | 23 | |
| 11.6 | 7.63 | 1 | |
| 13.4 | 6.61 | 74 | |
| 14.2 | 6.24 | 4 | |
| 15.4 | 5.75 | 45 | |
| 16.6 | 5.34 | 21 | |
| 17.0* | 5.22 | 2 | |
| 18.0 | 4.93 | 6 | |
| 19.6 | 4.53 | 26 | |
| 20.4 | 4.35 | 91 | |
| 21.3 | 4.17 | 39 | |
| 21.8* | 4.08 | 7 | (sh) |
| 22.4 | 3.97 | 4 | |
| 23.2 | 3.83 | 30 | |
| 23.7 | 3.75 | 25 | |
| 25.3 | 3.520 | 18 | |
| 26.8 | 3.326 | 31 | |
| 27.3* | 3.267 | 15 | |
| 28.1* | 3.175 | 3 | |
| 28.7 | 3.110 | 11 | |
| 30.5 | 2.931 | 7 | (sh) |
| 31.1 | 2.876 | 30 | |
| 31.7 | 2.823 | 47 | |
| 33.4 | 2.683 | 18 | |
| 35.1* | 2.557 | 1 | |
| 35.8* | 2.508 | 9 | |
| 36.2 | 2.481 | 2 | (sh) |
| 37.9* | 2.374 | 2 | |
| 39.2* | 2.298 | 3 | |
| 39.7* | 2.270 | 4 | |
| 40.3 | 2.238 | 2 | |
| 40.8* | 2.212 | 1 | |
| 42.0* | 2.151 | 1 | |
| 42.6* | 2.122 | 1 | |
| 43.6 | 2.076 | 4 | |
| 44.3* | 2.045 | 1 | |
| 45.6 | 1.989 | 3 | |
| 46.5* | 1.953 | 2 | |
| 47.5* | 1.914 | 1 | |
| 48.6* | 1.873 | 1 | |
| 49.5 | 1.841 | 11 | |
| 49.8 | 1.831 | 2 | (sh) |
| 50.3* | 1.814 | 2 | |
| 52.0 | 1.759 | 5 | |
| 53.8 | 1.704 | 2 | |
| 55.3 | 1.661 | 9 | |

\* = line possibly attributable to an impurity
(sh) = shoulder (c) Adsorption capacities were measured on the product of part (a) after calcination in air for 2 hours at 600° C. using a standard McBain-Bakr gravimetric adsorption apparatus. The following data were obtained on a sample activated at 350° C.:

| Absorbate | Kinetic Diameter, A | Pressure Torr | Temp.,°C. | Wt. % Adsorbed |
|---|---|---|---|---|
| O$_2$ | 3.46 | 101 | −183 | 13.3 |
| O$_2$ | 3.46 | 739 | −183 | 13.9 |
| n-Hexane | 4.3 | 53 | 24.8 | 13.0 |
| H$_2$O | 2.65 | 4.6 | 23.9 | 14.1 |
| H$_2$O | 2.65 | 19 | 24.3 | 15.5 |

(d) The as-synthesized 276 hour digested FAPO-17 product of part (a) supra was calcined in air for 2 hours at 600° C. The X-ray powder diffraction pattern of the calcined product was characterized by the following data:

TABLE M

| 2θ | d, (A) | 100 × I/I$_o$ |
|---|---|---|
| 7.7 | 11.48 | 68 |
| 9.7 | 9.12 | 43 |

TABLE M-continued

| 2θ | d, (A) | 100 × I/I_o |
|---|---|---|
| 11.8 | 7.50 | 12 |
| 13.4 | 6.61 | 100 |
| 14.1 | 6.28 | 30 |
| 14.6 | 6.07 | 3 |
| 15.4 | 5.75 | 16 |
| 16.5 | 5.37 | 4 |
| 17.8 | 4.98 | 4 |
| 19.5 | 4.55 | 10 |
| 20.4 | 4.35 | 57 |
| 21.3 | 4.17 | 21 |
| 21.7* | 4.10 | 4 (sh) |
| 22.4 | 3.97 | 3 |
| 23.3 | 3.82 | 3 (sh) |
| 23.7 | 3.75 | 29 |
| 24.1* | 3.69 | 3 |
| 24.7* | 3.60 | 12 |
| 25.0 | 3.562 | 12 |
| 25.9* | 3.440 | 9 |
| 26.9 | 3.314 | 18 |
| 28.0 | 3.187 | 21 |
| 28.6 | 3.121 | 16 |
| 29.4* | 3.038 | 13 |
| 29.8* | 2.998 | 14 |
| 31.2 | 2.867 | 23 |
| 31.6 | 2.831 | 23 |
| 33.4 | 2.683 | 8 |
| 34.6 | 2.592 | 3 |
| 35.8* | 2.508 | 8 (sh) |
| 36.1 | 2.488 | 8 (sh) |
| 38.6 | 2.332 | 1 |
| 40.8 | 2.210 | 1 |
| 41.6 | 2.171 | 1 |
| 47.2 | 1.926 | 3 |
| 48.3 | 1.884 | 1 |
| 48.8 | 1.866 | 4 |
| 49.8 | 1.831 | 3 |
| 50.8 | 1.797 | 3 |
| 52.8 | 1.734 | 1 |
| 55.6 | 1.653 | 6 |

\* = line possibly attributable to an impurity
(sh) = shoulder

The species FAPO-17 as referred to herein is a ferroaluminophosphate material having a three-dimensional microporous crystal framework structure of the tetrahedral units, $PO_2^+$, $AlO_2^-$ and at least one of $FeO_2^-$ and $FeO_2^{-2}$, and whose essential empirical chemical composition on an anhydrous basis is:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3, "x", "y" and "z" represent respectively, the mole fractions of iron, aluminum and phosphorus present in the oxide moiety, said mole fractions being within the compositional area bounded by points A, B, C, D and E on the ternary diagram which is FIG. 1, or preferably within the are bounded by points a, b, c, d and e on the ternary diagram which is FIG. 2, said ferroaluminophosphate having a characteristic X-ray powder diffraction pattern which contains at least the d-spacings set forth below in Table VII. In the form as synthesized in accordance with the process of this invention, "m" has a value of from 0.02 to 0.30.

TABLE VII

| 2θ | d (A) | Relative Intensity |
|---|---|---|
| 7.7–7.8 | 11.48–11.33 | m–vs |
| 9.7–9.8 | 9.12–9.03 | m |
| 13.4 | 6.61 | m–vs |
| 15.4 | 5.75 | w–m |
| 19.4–19.7 | 4.58–4.51 | w–m |
| 20.4 | 4.35 | m–vs |
| 21.3 | 4.17 | m |
| 31.6–31.7 | 2.814–2.822 | m |

All of the as-synthesized FAPO-17 compositions for which x-ray powder diffraction data have presently been obtained have patterns which are within the generalized pattern of Table VIII below.

TABLE VIII

| 2θ | d, (A) | 100 × I/I_o |
|---|---|---|
| 7.7–7.8 | 11.48–11.33 | 68–100 |
| 9.7–9.8 | 9.12–9.03 | 23–43 |
| 11.6–11.8 | 7.63–7.50 | 1–12 |
| 13.4 | 6.61 | 74–100 |
| 14.1–14.2 | 6.28–6.24 | 4–30 |
| 14.6 | 6.07 | 0–3 |
| 15.4 | 5.75 | 16–45 |
| 16.5–16.6 | 5.37–5.34 | 4–21 |
| 17.8–18.0 | 4.98–4.93 | 4–6 |
| 19.5–19.6 | 4.55–4.53 | 10–26 |
| 20.4 | 4.35 | 57–91 |
| 21.3 | 4.17 | 21–39 |
| 21.7–21.8 | 4.10–4.08 | 4–7 (sh) |
| 22.4 | 3.97 | 2–4 |
| 23.2–23.3 | 3/83–3.82 | 3–30 |
| 23.7 | 3.75 | 25–29 |
| 25.0–25.3 | 3.562–3.520 | 12–18 |
| 26.8–26.9 | 3.326–3.314 | 18–31 |
| 27.3 | 3.267 | 0–15 |
| 28.0–28.1 | 3.187–3.175 | 3–21 |
| 28.6–28.7 | 3.121–3.110 | 11–16 |
| 29.4 | 3.038 | 0–13 |
| 29.8 | 2.998 | 0–14 |
| 30.5 | 2.931 | 7 (sh) |
| 31.1–31.2 | 2.876–2.867 | 23–30 |
| 31.6–31.7 | 2.831–2.823 | 23–47 |
| 33.4 | 2.683 | 8–18 |
| 34.6 | 2.592 | 0–3 |
| 35.1 | 2.557 | 0–1 |
| 35.8 | 2.508 | 8–9 |
| 36.1–36.2 | 2.488–2.481 | 2–8 (sh) |
| 37.9 | 2.374 | 0–2 |
| 38.6 | 2.332 | 0–1 |
| 39.2 | 2.298 | 0–3 |
| 39.7 | 2.270 | 0–4 |
| 40.3 | 2.238 | 0–2 |
| 40.8 | 2.212 | 0–1 |
| 42.0 | 2.151 | 0–1 |
| 42.6 | 2.122 | 0–1 |
| 43.6 | 2.076 | 0–4 |
| 44.3 | 2.045 | 0–1 |
| 45.6 | 1.989 | 0–3 |
| 46.5 | 1.953 | 0–2 |
| 47.2–47.5 | 1.926–1.914 | 1–3 |
| 48.3 | 1.884 | 0–1 |
| 48.6–48.8 | 1.873–1.866 | 1–4 |
| 49.5 | 1.841 | 0–11 |
| 49.8 | 1.831 | 2–3 |
| 50.3–50.8 | 1.814–1.797 | 2–3 |
| 52.0 | 1.759 | 0–5 |
| 53.8 | 1.704 | 0–4 |
| 55.6 | 1.653 | 0–6 |

EXAMPLE 8

(Preparation of FAPO-18)

(a) Using Method (a), a reaction gel was prepared having a composition, expressed in terms of molar oxide ratios, of:

1.0TEAOH:0.1Fe$_2$O$_3$:0.9Al$_2$O$_3$:P$_2$O$_5$:40H$_2$O

The reagents employed and quantity of each were: 2.2 grams α iron oxyhydroxide [αFe(III)OOH]; 15.5 grams hydrated aluminum oxide; 28.8 grams of 85% aqueous ortho-phosphoric acid; 47.2 grams water and 46.0 grams of 40% aqueous solution of tetraethylammonium hydroxide (TEAOH). The gel was divided into two equal portions. One portion was crystallized for 25.5 hours at 200° C. and the other portion for 25.5 hours at 150° C. By X-ray analysis, the solid product resulting from the 200° C. crystallization was substantially pure FAPO-18, whereas the product of the portion crystallized at 150° C. was principally FAPO-5 with only a trace amount of FAPO-18. By chemical analysis the chemical composition of the FAPO-18 product was:

0.05TEAOH:(Fe$_{0.06}$Al$_{0.50}$P$_{0.44}$)O$_2$:0.21H$_2$O

The X-ray powder diffraction pattern of this product was characterized by the following data:

TABLE O

| 2θ | d, (A) | 100 × I/I$_o$ |
|---|---|---|
| 9.7 | 9.12 | 100 |
| 10.6 | 8.35 | 10 |
| 11.2 | 7.90 | 5 |
| 13.3 | 6.66 | 5 |
| 14.2 | 6.24 | 5 |
| 14.9 | 5.95 | 10 |
| 15.7 | 5.64 | 30 |
| 17.2 | 5.16 | 1 |
| 18.0 | 4.93 | 25 |
| 19.6 | 4.53 | 10 |
| 20.3 | 4.37 | 40 |
| 21.2 | 4.19 | 65 |
| 22.2 | 4.00 | 15 |
| 23.6 | 3.77 | 5 |
| 24.1 | 3.69 | 5 |
| 24.6 | 3.62 | 10 |
| 25.1 | 3.548 | 5 |
| 25.7 | 3.466 | 5 |
| 26.4 | 3.376 | 20 |
| 26.6 | 3.351 | 10 (sh) |
| 27.0 | 3.302 | 15 |
| 28.2 | 3.164 | 20 |
| 29.2* | 3.058 | 5 |
| 30.2 | 2.959 | 25 |
| 31.0 | 2.885 | 15 |
| 31.4 | 2.849 | 15 |
| 31.9 | 2.805 | <5 |
| 32.6 | 2.747 | 25 |
| 33.4 | 2.683 | 15 |
| 34.8 | 2.578 | 10 |
| 36.2 | 2.481 | 5 (sh) |
| 36.8* | 2.442 | 20 |
| 40.2 | 2.243 | 5 |
| 41.3 | 2.186 | 5 |
| 43.1 | 2.100 | 5 |

* = line possibly attributable to an impurity
(sh) = shoulder (b) A portion of the as-synthesized FAPO-18 product of part (a) was calcined at 500° C. for 2.75 hours in a nitrogen atmosphere. The X-ray powder diffraction pattern of the calcined product was characterized by the following data:

TABLE P

| 2θ | d, (A) | 100 33 I/I$_o$ |
|---|---|---|
| 9.517 | 9.2928 | 100.0 |
| 9.974* | 8.8681 | 22.9 |
| 10.613 | 8.3352 | 12.8 |
| 12.929 | 6.8471 | 10.0 |
| 13.492* | 6.5625 | 4.0 |
| 14.012 | 6.3202 | 2.0 |

TABLE P-continued

| 2θ | d, (A) | 100 33 I/I$_o$ |
|---|---|---|
| 16.089 | 5.5085 | 7.9 |
| 16.915 | 5.2415 | 15.7 |
| 17.197 | 5.1562 | 12.2 |
| 19.079* | 4.6517 | 2.3 |
| 19.648 | 4.5181 | 2.5 |
| 20.020 | 4.4349 | 3.4 |
| 20.682* | 4.2946 | 7.8 |
| 21.358 | 4.1601 | 7.5 |
| 23.909 | 3.7217 | 8.3 |
| 26.018 | 3.4246 | 3.3 |
| 26.263 | 3.3932 | 4.5 |
| 27.812 | 3.2077 | 3.5 |
| 30.068 | 2.9720 | 2.7 |
| 30.414 | 2.9389 | 4.2 |
| 30.759 | 2.9067 | 2.3 |
| 31.148 | 2.8713 | 4.7 |
| 32.194 | 2.7804 | 5.2 |
| 32.526 | 2.7527 | 2.1 |
| 32.702 | 2.7583 | 3.1 |
| 33.189 | 2.6992 | 6.6 |
| 33.572* | 2.6693 | 1.5 |
| 35.696 | 2.5152 | 6.8 |
| 40.779* | 2.2127 | 1.6 |
| 41.078* | 2.1972 | 1.6 |
| 48.909 | 1.8622 | 2.0 |
| 49.114* | 1.8549 | 2.6 |
| 49.285* | 1.8489 | 2.3 |
| 49.498 | 1.8414 | 2.6 |
| 49.900* | 1.8275 | 1.8 |
| 50.205* | 1.8171 | 3.0 |
| 54.086 | 1.6955 | 1.7 |
| 54.183 | 1.6927 | 2.8 |

* = line possibly attributable to an impurity (c) A portion of the calcined material of part (b) supra was utilized in adsorption capacity studies using a standard McBain-Bakr gravimetric adsorption apparatus. Measurements were made on a sample after vacuum activation at 350° C. The following data were obtained:

| Adsorbate | Kinetic Diameter, A | Pressure Torr | Temp., °C. | Wt. % Absorbed |
|---|---|---|---|---|
| O$_2$ | 3.46 | 103 | −183 | 18.9 |
| O$_2$ | 3.46 | 733 | −183 | 25.2 |
| n-Hexane | 4.3 | 51 | 23.4 | 8.8 |
| i-Butane | 5.0 | 100 | 23.0 | 2.0 |
| H$_2$O | 2.65 | 4.6 | 22.9 | 23.6 |
| H$_2$O | 2.65 | 19.5 | 23.0 | 35.2 |

EXAMPLE 9

(Preparation of FAPO-18)

(a) A reaction mixture having a composition, expressed in terms of molar oxide ratios, of:

2.0TEAOH:0.2Fe$_2$O$_3$:0.8Al$_2$O$_3$:P$_2$O$_5$:121H$_2$O was prepared by combining, using mixing Method (d), 3.5 grams of anhydrous iron (II) acetate [Fe(II)(OAc)$_2$]; 16.4 grams of aluminum isopropoxide; 11.6 grams of an 85% aqueous ortho-phosphoric acid; 80.0 grams of water and 36.8 grams of a 40% aqueous solution of tetraethylammonium hydroxide. A portion of the gel was crystallized at 150° C. for 42 hours. By X-ray analysis the solid product was determined to be substantially pure FAPO-18. The X-ray powder diffraction pattern was characterized by the following data:

TABLE Q

| 2θ | d, (A) | 100 × I/I₀ |
|---|---|---|
| 9.6 | 9.21 | 100 |
| 10.4 | 8.51 | 7 |
| 11.0 | 8.04 | 9 |
| 13.2 | 6.71 | 5 |
| 14.1 | 6.28 | 8 |
| 14.9 | 5.95 | 9 |
| 15.6 | 5.68 | 10 |
| 17.0 | 5.22 | 26 |
| 17.9 | 4.96 | 11 (sh) |
| 18.3* | 4.85 | 5 (sh) |
| 18.6* | 4.77 | 4 (sh) |
| 20.2 | 4.40 | 24 |
| 21.0 | 4.23 | 44 |
| 22.1 | 4.02 | 13 |
| 23.3 | 3.82 | 3 |
| 23.9 | 3.72 | 3 |
| 24.4 | 3.65 | 9 |
| 24.9 | 3.58 | 3 |
| 25.4 | 3.506 | 3 |
| 26.1 | 3.414 | 11 |
| 26.5 | 3.363 | 5 |
| 26.8* | 3.326 | 9 |
| 27.4* | 3.255 | 1 |
| 28.1 | 3.175 | 7 |
| 29.1* | 3.069 | 2 |
| 30.0 | 2.979 | 14 |
| 30.8 | 2.903 | 11 |
| 31.3 | 2.858 | 11 |
| 31.8 | 2.814 | 2 (sh) |
| 32.4 | 2.763 | 4 |
| 33.4 | 2.683 | 3 |
| 34.5 | 2.600 | 3 |
| 35.8 | 2.508 | 3 |
| 36.2 | 2.481 | 3 |
| 40.0 | 2.254 | 1 |
| 43.0 | 2.103 | 5 |
| 44.1* | 2.053 | 1 |
| 47.8 | 1.983 | 1 |
| 49.4 | 1.845 | 3 |
| 49.9 | 1.828 | 4 |
| 51.0 | 1.791 | 4 |
| 54.2 | 1.692 | 4 |
| 55.2* | 1.664 | 2 |

\* = line possibly attributable to an impurity
(sh) = shoulder (b) A portion of the as-synthesized product of part (a) above was calcined in air at 500° C. for 2.75 hours. The X-ray powder diffraction pattern of the calcined product indicated that partial decomposition of the sample had occurred with the probable formation of crystalline impurities. The X-ray pattern was characterized by the following data:

TABLE R

| 2θ | d, (A) | 100 × I/I₀ |
|---|---|---|
| 9.4 | 9.41 | 100 |
| 9.9* | 8.93 | 67 (sh) |
| 10.3 | 8.59 | 6 (sh) |
| 12.8 | 6.92 | 19 |
| 13.7 | 6.46 | 10 |
| 15.7 | 5.64 | 13 |
| 16.9 | 5.25 | 26 |
| 18.0 | 4.93 | 8 |
| 20.5 | 4.33 | 16 |
| 21.6 | 4.11 | 11 |
| 22.2 | 4.00 | 4 |
| 22.8* | 3.90 | 4 |
| 23.6 | 3.77 | 19 |
| 24.3 | 3.66 | 10 |
| 24.8 | 3.59 | 4 |
| 26.1 | 3.414 | 16 |
| 27.1 | 3.290 | 3 |
| 28.6 | 3.121 | 6 |
| 30.4 | 2.940 | 16 |
| 31.5 | 2.840 | 16 |
| 32.1 | 2.788 | 13 |
| 33.0 | 2.715 | 13 |
| 35.7 | 2.515 | 3 |
| 41.0* | 2.201 | 8 |
| 43.0 | 2.103 | 7 |
| 48.9* | 1.863 | 13 |
| 50.0* | 1.824 | 8 |
| 55.2* | 1.664 | 8 |

\* = line possibly attributable to an impurity
(sh) shoulder (c) The remaining portion of the gel from part (a) was crystallized at 200° C., for 107 hours and was found by X-ray analysis to have produced FAPO-18 in admixture with a trace amount of FAPO-5. The chemical composition of the as-synthesized product in terms of moles of TEAOH per average TO₂ unit, was:

$$0.06\text{TEAOH}:(\text{Fe}_{0.09}\text{Al}_{0.44}\text{P}_{0.47})\text{O}_2:0.14\text{H}_2\text{O}$$

The species FAPO-18 as referred to herein is ferroaluminophosphate material having a three-dimensional microporous crystal framework structure of the tetrahedral units $PO_2^+$, $AlO_2^-$ and at least one of $FeO_2^-$ and $FeO_2^{-2}$, and whose essential empirical chemical composition on an anhydrous basis is:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3, "x", "y" and "z" represent respectively, the mole fractions of iron, aluminum and phosphorus present in the oxide moiety, said mole fractions being within the compositional area bounded by points A, B, C, D and E on the ternary diagram which is FIG. 1, or preferably within the area bounded by points a, b, c, d and e on the ternary diagram which is FIG. 2, said ferroaluminophosphate having a characteristic X-ray powder diffraction pattern which contains at least the d-spacings set forth below in Table IX. In the form as synthesized in accordance with the process of this invention. "m" has a value of from 0.02 to 0.30.

TABLE IX

| 2θ | d (A) | Relative Intensity |
|---|---|---|
| 9.4–9.7 | 9.41–9.12 | vs |
| 15.6–16.1 | 5.68–5.51 | w–m |
| 16.9–17.2 | 5.25–5.16 | w–s |
| 20.2–20.7 | 4.40–4.29 | w–m |
| 21.0–21.6 | 4.23–4.11 | w–m |

All of the as-synthesized FAPO-18 compositions for which X-ray powder diffraction data have presently been obtained have patterns which are within the generalized pattern of Table T below:

TABLE X

| 2θ | d, (A) | 100 × I/I₀ |
|---|---|---|
| 9.4–9.7 | 9.41–9.12 | 100 |
| 10.3–10.6 | 8.59–8.34 | 6–7 |
| 11.0–11.2 | 8.04–7.90 | 0–9 |
| 12.8–13.3 | 6.92–6.66 | 5–19 |
| 13.7–14.2 | 6.46–6.24 | 8–16 |
| 14.9 | 5.95 | 0–9 |
| 15.6–16.1 | 5.68–5.51 | 8–30 |
| 16.9–17.2 | 5.25–5.16 | 0–26 |
| 17.9–18.0 | 4.96–4.93 | 0–25 |

TABLE X-continued

| 2θ | d, (A) | 100 × I/I₀ |
|---|---|---|
| 19.6-20.0 | 4.53-4.43 | 3-10 |
| 20.2-20.7 | 4.40-4.29 | 16-40 |
| 21.0-21.6 | 4.23-4.11 | 8-44 |
| 22.1-22.2 | 4.02-4.00 | 0-15 |
| 23.3-23.6 | 3.82-3.77 | 3-19 |
| 23.9-24.1 | 3.72-3.69 | 3-8 |
| 24.3-24.6 | 3.66-3.62 | 0-10 |
| 24.8-25.1 | 3.590-3.548 | 0-5 |
| 24.4-25.7 | 3.506-3.466 | 0-5 |
| 26.0-26.1 | 3.425-3.414 | 0-16 |
| 26.3-26.5 | 3.393-3.363 | 0-20 |
| 27.8-28.2 | 3.208-3.164 | 0-20 |
| 30.0-30.4 | 2.979-2.940 | 3-25 |
| 30.8-31.0 | 2.907-2.885 | 2-15 |
| 31.1-31.5 | 2.871-2.840 | 5-16 |
| 31.8-32.2 | 2.814-2.780 | 2-13 |
| 32.4-32.6 | 2.763-2.747 | 4-25 |
| 32.7-33.0 | 2.738-2.715 | 0-13 |
| 33.2-33.4 | 2.699-2.683 | 0-15 |
| 34.5-34.8 | 2.600-2.578 | 0-10 |
| 35.7-36.2 | 2.508-2.481 | 0-7 |
| 40.0-40.2 | 2.254-2.243 | 0-5 |
| 41.3 | 2.186 | 5 |
| 43.0-43.1 | 2.103-2.100 | 0-7 |
| 47.8 | 1.903 | 1 |
| 49.4-49.5 | 1.845-1.841 | 3 |
| 51.0 | 1.791 | 4 |
| 54.1-54.2 | 1.696-1.692 | 3-4 |

EXAMPLE 10

(Preparation of FAPO-34)

(a) A reaction gel consisting of 23.2 grams of anhydrous iron (II) acetate [Fe(II)(OAc)₂], 108.9 grams of aluminum isopropoxide, 76.9 grams of 85% aqueous ortho-phosphoric acid, 123.7 grams of water and 245.5 grams of a 40% aqueous solution of tetraethylammonium hydroxide (TEAOH) was prepared using mixing Method (c). The composition of the reaction mixture in terms of molar oxide ratios was:

$$2.0\text{TEAOH}:0.2\text{Fe}_2\text{O}_3:0.8\text{Al}_2\text{O}_3:\text{P}_2\text{O}_5:50\text{H}_2\text{O}$$

Half of the gel was crystallized at 200° C. for 117 hours. By chemical analysis the recovered solid product was found to have a chemical composition in terms of moles of TEAOH per average $TO_2$ unit of:

$$0.07\text{TEAOH}:(\text{Fe}_{0.08}\text{Al}_{0.44}\text{P}_{0.48})\text{O}_2:0.29\text{H}_2\text{O}$$

The X-ray powder diffraction pattern of the as-synthesized product was characterized by the following data:

TABLE S

| 2θ | d, (A) | 100 × I/I₀ |
|---|---|---|
| 7.3* | 12.11 | 1 |
| 9.6 | 9.21 | 100 |
| 12.9 | 6.86 | 11 |
| 14.2 | 6.24 | 11 |
| 16.1 | 5.50 | 23 |
| 18.2 | 4.87 | 15 |
| 20.7 | 4.29 | 59 |
| 22.4 | 3.97 | 3 |
| 23.3 | 3.82 | 1 |
| 25.5 | 3.493 | 16 |
| 26.1 | 3.414 | 13 |
| 27.2* | 3.278 | 4 |
| 27.7 | 3.220 | 2 |
| 28.6 | 3.121 | 2 |
| 29.8 | 2.998 | 3 (sh) |
| 30.7 | 2.912 | 20 |
| 31.5 | 2.840 | 14 |

TABLE S-continued

| 2θ | d, (A) | 100 × I/I₀ |
|---|---|---|
| 34.6 | 2.592 | 5 |
| 36.5 | 2.462 | 2 |
| 39.8 | 2.265 | 2 |
| 43.7* | 2.071 | 3 |
| 47.8 | 1.903 | 2 |
| 49.4 | 1.845 | 4 |
| 50.7 | 1.801 | 2 |
| 51.4 | 1.778 | 2 |
| 53.3 | 1.719 | 2 |

\* = line possibly attributable to an impurity
(sh) = shoulder (b) The remaining portion of the gel from part (a) of this Example was crystallized for 117 hours at 125° C. By X-ray analysis the solid product was found to be FAPO-34 having an X-ray powder pattern essentially identical to that of Table S, supra.

(c) A portion of the FAPO-34 composition of part (a) was calcined for 2 hours at 450° C. in a nitrogen atmosphere. The X-ray powder diffraction pattern of the calcined product was characterized by the following data:

TABLE T

| 2θ | d, (A) | 100 × I/I₀ |
|---|---|---|
| 9.4 | 9.41 | 100 |
| 10.1* | 8.76 | 2 (sh) |
| 12.8 | 6.92 | 20 |
| 13.8 | 6.42 | 2 |
| 15.9 | 5.57 | 12 |
| 16.9* | 5.25 | 1 (sh) |
| 17.7 | 5.01 | 7 |
| 18.9 | 4.70 | 2 |
| 19.6 | 4.53 | 2 (sh) |
| 20.5 | 4.06 | 21 |
| 21.9 | 4.33 | 1 |
| 22.3 | 3.99 | 1 |
| 23.0 | 3.87 | 2 |
| 24.0* | 3.71 | 1 (sh) |
| 24.9 | 3.58 | 6 |
| 25.8 | 3.453 | 6 |
| 27.4 | 3.255 | 2 |
| 28.0 | 3.187 | 2 |
| 29.0* | 3.079 | 1 |
| 29.5 | 3.028 | ε1 |
| 30.5 | 2.931 | 13 |
| 30.9* | 2.894 | 4 (sh) |
| 31.5 | 2.840 | 1 (sh) |
| 32.2 | 2.780 | 1 |
| 33.3 | 2.691 | 1 |
| 34.4 | 2.607 | 2 |
| 35.9 | 2.501 | 2 |
| 38.5 | 2.338 | 1 |
| 38.9 | 2.315 | 1 |
| 42.7 | 2.118 | 1 |
| 43.3 | 2.090 | 1 |
| 47.5 | 1.914 | 1 |
| 48.7 | 1.870 | 2 |
| 50.6 | 1.804 | 2 |
| 53.0 | 1.728 | 1 |
| 54.2 | 1.692 | 1 |
| 55.8 | 1.647 | 1 |

\* = line possibly attributable to an impurity
(sh) = shoulder (d) Adsorption capacities were measured on a portion of part (a) which had been calcined for 1.25 hours at 600° C. A standard McBain-Bakr gravimetric adsorption apparatus was employed. The following data were obtained on a sample activated at 350° C.:

| Absorbate | Kinetic Diameter, A | Pressure Torr | Temp., °C. | Wt. % Adsorbed |
|---|---|---|---|---|
| Oxygen | 3.46 | 100 | −183 | 22.8 |
| Oxygen | 3.46 | 734 | −183 | 32.3 |
| n-Hexane | 4.3 | 51 | 24.3 | 10.4 |
| H$_2$O | 2.65 | 4.6 | 24.4 | 28.3 |
| H$_2$O | 2.65 | 18.5 | 24.0 | 32.7 |

EXAMPLE 11

(Preparation of FAPO-34)

Using mixing Method (c), 5.6 grams of ferrous sulfate heptahydrate [Fe(SO$_4$).7H$_2$O]; 16.4 grams of aluminum isopropoxide; 11.6 grams of an 85% aqueous ortho-phosphoric acid solution; 35 grams of water; and 36.8 grams of a 40% aqueous tetraethylammonium hydroxide solution (TEAOH) were combined to form a reaction mixture having the following composition in terms of molar oxide ratios:

2.0TEAOH:0.2Fe$_2$O$_3$:0.8Al$_2$O$_3$:P$_2$O$_5$:68H$_2$O

The reaction mixture was crystallized at 200° C. for 42 hours. The solid product was found to have an X-ray powder diffraction pattern essentially identical to that of Table S, supra.

The species FAPO-34 as referred to herein is a ferroaluminophosphate material having a three-dimensional microporous crystal framework structure of the tetrahedral units PO$_2^+$, AlO$_2^-$ and at least one of FeO$_2^-$ and FeO$_2^{-2}$ and whose essential empirical chemical composition on an anhydrous basis is:

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, "x", "y" and "z" represent respectively, the mole fractions of iron, aluminum and phosphorus present in the oxide moiety, said mole fractions being within the compositional area bounded by points A, B, C and D on the ternary diagram which is FIG. 1, or preferably within the area bounded by points a, b, c, and d on the ternary diagram which is FIG. 2, said ferroaluminophosphate having a characteristic X-ray powder diffraction pattern which contains at least the d-spacings set forth below in Table XI. In the form as synthesized in accordance with the process of this invention, "m" has a value of from 0.02 to 0.3.

TABLE XI

| 2θ | d (A) | Relative Intensity |
|---|---|---|
| 9.4–9.6 | 9.41–9.21 | vs |
| 12.8–12.9 | 6.92–6.86 | w–m |
| 15.9–16.1 | 5.57–5.50 | w–m |
| 20.5–20.7 | 4.33–4.29 | m |
| 30.5–30.8 | 2.931–2.903 | w–m |

All of the as-synthesized FAPO-34 compositions for which X-ray powder diffraction data have presently been obtained have patterns which are within the generalized pattern of Table XII below:

TABLE XII

| 2θ | d, (A) | 100 × I/I$_o$ |
|---|---|---|
| 9.4–9.6 | 9.41–9.2 | 100 |
| 12.8–12.9 | 6.92–6.86 | 11–20 |
| 13.8–14.2 | 6.42–6.24 | 2–11 |
| 15.9–16.1 | 5.57–5.50 | 12–23 |
| 17.7–18.2 | 5.01–4.87 | 7–15 |
| 18.9 | 4.70 | 0–2 |
| 19.6 | 4.53 | 2 (sh) |
| 20.5–20.7 | 4.33–4.29 | 24–59 |
| 21.9 | 4.06 | 0–1 |
| 22.3–22.4 | 3.99–3.97 | <1–3 |
| 23.0–23.3 | 3.87–3.82 | 1–3 |
| 24.9–25.5 | 3.58–3.493 | 6–16 |
| 25.8–26.1 | 3.453–3.414 | 6–13 |
| 27.4–27.7 | 3.255–3.220 | 2 |
| 28.0–28.6 | 3.187–3.121 | 2 |
| 29.5–29.8 | 3.028–2.998 | <1–3 (sh) |
| 30.5–30.8 | 2.912–2.903 | 13–20 |
| 31.5 | 2.840 | 1–14 (sh) |
| 32.2 | 2.780 | 0–1 |
| 33.3 | 2.691 | 0–1 |
| 34.4–34.6 | 2.607–2.592 | 2–5 |
| 35.9–36.5 | 2.501–2.462 | 2 |
| 38.5 | 2.338 | 0–1 |
| 38.9 | 2.315 | 0–1 |
| 39.5–3.98 | 2.281–2.265 | 1–2 |
| 42.7 | 2.118 | 0–1 |
| 43.3–43.4 | 2.090–2.085 | 1 |
| 47.5–47.8 | 1.914–1.903 | 1–2 |
| 48.7–49.4 | 1.870–1.845 | 2–4 |
| 50.6–50.7 | 1.804–1.801 | 2 |
| 51.4 | 1.778 | 2 |
| 53.0–53.4 | 1.728–1.719 | 1–2 |
| 54.2–54.8 | 1.692–1.675 | <1–2 |
| 55.8 | 1.647 | 0–1 |

(sh) = shoulder

EXAMPLE 12

(Preparation of FAPO-35)

(a) Using mixing Method (a), a reaction mixture having the composition (in terms of molar oxide ratios) of:

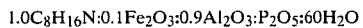

was prepared by combining 3.5 grams of anhydrous iron (II) acetate; 37.8 grams of aluminum isopropoxide, 23.1 grams of 85% ortho-phosphoric acid, 46.6 grams of water and 57.1 grams of 25.1% aqueous methylquinuclidine (C$_8$H$_{16}$N). Half of the resulting gel was crystallized at 150° C. for 66 hours. The resulting solid product (FAPO-35) had a chemical composition of

and an X-ray powder diffraction pattern characterized by the following data:

TABLE U

| 2θ | d, (A) | 100 × I/I$_o$ |
|---|---|---|
| 8.0* | 11.05 | 15 |
| 8.7 | 10.16 | 13 |
| 9.8* | 9.03 | 4 |
| 11.0 | 8.04 | 52 |
| 11.4 | 7.76 | 4 (sh) |
| 13.5 | 6.56 | 29 |
| 15.7 | 5.64 | 8 |
| 16.1 | 5.50 | 8 |
| 17.5 | 5.07 | 70 |
| 18.0 | 4.93 | 10 (sh) |
| 18.7* | 4.75 | 18 |
| 20.6* | 4.31 | 10 (sh) |
| 21.1 | 4.21 | 32 |
| 22.1 | 4.02 | 100 |
| 23.4 | 3.80 | 29 (sh) |

TABLE U-continued

| 2θ | d, (A) | 100 × I/I₀ |
|---|---|---|
| 25.2 | 3.534 | 7 |
| 25.5* | 3.493 | 4 |
| 26.5* | 3.363 | 4 (sh) |
| 27.1* | 3.290 | 33 |
| 28.7 | 3.110 | 39 |
| 29.4* | 3.038 | 16 |
| 32.0 | 2.979 | 4 (sh) |
| 32.5 | 2.755 | 34 |
| 34.7 | 2.585 | 6 |
| 36.0 | 2.495 | 3 |
| 38.0 | 2.368 | 3 |
| 48.2 | 1.888 | 3 |
| 49.0 | 1.859 | 4 |
| 51.9 | 1.762 | 3 |

\* = line possibly attributable to an impurity
(sh) = shoulder (b) The remaining half of the gel from part (a) of this Example was crystallized for 66 hours at 200° C. and resulted in a FAPO-35 composition having essentially the same X-ray pattern as in Table U, supra.

(c) A sample of FAPO-35 prepared in essentially the same manner as set forth in part (a) above except for a crystallization period of 228 hours, was calcined at 500° C. for 2 hours in a nitrogen atmosphere. The X-ray powder diffraction pattern of the calcined product was characterized by the following data:

TABLE W

| 2θ | d, (A) | 100 × I/I₀ |
|---|---|---|
| 8.0* | 11.05 | 11 |
| 8.6 | 10.28 | 22 |
| 9.5* | 9.31 | 6 |
| 10.9 | 8.12 | 83 |
| 11.4 | 7.76 | 5 (sh) |
| 12.3* | 7.20 | 2 |
| 13.4 | 6.61 | 59 |
| 15.8 | 5.61 | 9 |
| 16.0* | 5.54 | 3 |
| 17.4 | 5.10 | 65 |
| 17.8 | 4.98 | 3 |
| 18.6* | 4.77 | 4 |
| 18.9* | 4.70 | 7 |
| 20.9 | 4.25 | 42 |
| 22.1 | 4.02 | 100 |
| 22.9 | 3.88 | 9 |
| 23.4 | 3.80 | 35 |
| 24.9 | 3.58 | 28 |
| 25.4 | 3.506 | 12 |
| 26.6 | 3.351 | 16 |
| 27.1* | 3.290 | 20 |
| 28.4 | 3.143 | 38 |
| 29.3* | 3.048 | 9 |
| 31.4 | 2.849 | 8 |
| 32.3 | 2.772 | 37 |
| 32.8 | 2.730 | 3 |
| 34.3 | 2.614 | 8 |
| 35.1 | 2.557 | 6 |
| 36.0 | 2.495 | 9 |
| 37.8 | 2.380 | 3 |
| 38.3 | 2.350 | 2 |
| 39.7 | 2.270 | 2 |
| 40.3 | 2.238 | 1 |
| 41.2 | 2.191 | 2 |
| 42.0 | 2.151 | 5 |
| 42.6 | 2.122 | 4 |
| 44.8 | 2.023 | 2 |
| 46.7 | 1.945 | 3 |
| 47.3 | 1.922 | 3 |
| 48.6 | 1.873 | 5 |
| 49.8 | 1.831 | 4 |
| 51.2 | 1.784 | 6 |
| 55.7 | 1.650 | 5 |

\* = line possibly attributable to an impurity
(sh) = shoulder

The species FAPO-35 as referred to herein is a ferroaluminophosphate material having a three-dimensional microporous crystal framework structure of the tetrahedral units $PO_2^+$, $AlO_2^-$ and at least one of $FeO_2^-$ and $FeO_2^{-2}$, and whose essential empirical chemical composition on an anhydrous basis is:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3, "x", "y" and "z" represent respectively, the mole fractions of iron, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said ferroaluminophosphate having a characteristic X-ray powder diffraction pattern which contains at least the d-spacings set forth below in Table XIII. In the form as synthesized in accordance with the process of this invention, "m" has a value of from 0.02 to 0.3.

TABLE XIII

| 2θ | d (A) | Relative Intensity |
|---|---|---|
| 10.9–11.0 | 8.12–8.04 | m–s |
| 13.4–13.5 | 6.61–6.56 | m |
| 17.4–17.5 | 5.10–5.07 | s |
| 20.9–21.1 | 4.25–4.21 | m |
| 22.1 | 4.02 | vs |
| 28.4–28.7 | 3.143–3.110 | m |
| 32.3–32.5 | 2.775–2.772 | m |

All of the as-synthesized FAPO-35 compositions for which X-ray powder diffraction data have presently been obtained have patterns which are within the generalized pattern of Table XIV below:

TABLE XIV

| 2θ | d, (A) | 100 × I/I₀ |
|---|---|---|
| 8.6–8.7 | 10.28–10.16 | 13–22 |
| 10.9–11.0 | 8.12–8.04 | 52–83 |
| 11.4 | 7.76 | 0–5 (sh) |
| 13.4–13.5 | 6.61–6.56 | 29–59 |
| 15.7–15.8 | 5.64–5.61 | 8–9 |
| 17.4–17.5 | 5.10–5.07 | 65–70 |
| 17.8–18.0 | 4.98–4.93 | 3–10 (sh) |
| 20.9–21.1 | 4.25–4.21 | 32–42 |
| 21.1 | 4.02 | 100 |
| 22.9 | 3.88 | 0–9 |
| 23.4 | 3.80 | 29–35 (sh) |
| 24.9–25.2 | 3.58–3.53 | 7–28 |
| 25.4–25.5 | 3.506–3.493 | 4–12 |
| 26.5–26.6 | 3.363–3.351 | 4–16 (sh) |
| 27.1 | 3.290 | 20–33 |
| 28.4–28.7 | 3.143–3.110 | 38–39 |
| 29.3–29.4 | 3.048–3.034 | 0–16 |
| 31.4 | 2.849 | 0–8 |
| 32.0 | 2.979 | 0–4 |
| 32.3–32.5 | 2.772–2.755 | 34–37 |
| 32.8 | 2.730 | 0–3 |
| 34.3–34.7 | 2.614–2.585 | 6–8 |
| 35.1 | 2.557 | 0–6 |
| 36.0 | 2.495 | 3–9 |
| 37.8–38.0 | 2.380–2.368 | 3 |
| 38.3 | 2.350 | 0–2 |
| 39.7 | 2.270 | 0–2 |
| 40.3 | 2.238 | 0–<1 |
| 41.2 | 2.191 | 0–2 |
| 42.0 | 2.151 | 0–5 |
| 42.6 | 2.122 | 0–4 |

TABLE XIV-continued

| 2θ | d, (A) | 100 × I/I$_o$ |
|---|---|---|
| 44.8 | 2.023 | 0-2 |
| 46.7 | 1.945 | 0-3 |
| 47.3 | 1.922 | 0-3 |
| 48.2-48.6 | 1.888-1.873 | 3-5 |
| 49.0 | 1.859 | 0-4 |
| 49.8 | 1.831 | 0-4 |
| 51.2-51.9 | 1.784-1.761 | 3-6 |
| 55.7 | 1.650 | 5 |

As an indication of the catalytic activity, particularly the cracking activity, of the present class of novel ferroaluminophosphates organosilicates, certain of the FAPO species were tested for n-butane cracking using a bench-scale apparatus. The reactor was a cylindrical quartz tube 254 mm. in length and 10.3 mm. I.D. In each test the reactor was loaded with particles of the test FAPO which were 20–40 mesh (U.S. std.) in size and in an amount of from 0.5 to 5 grams, the quantity being selected so that the conversion of n-butane was at least 5% and not more than 90% under the test conditions. The FAPO samples had been previously calcined to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analyses of the feedstock and the reactor effluent were carried out using conventional gas chromatography techniques. The reactor effluent was analyzed after 10 minutes of on-stream operation. From the analytical data the pseudo-first-order rate constant ($k_a$) was calculated. Pertinent data is set forth in tabular form below.

| Sample of Example No. | Species | Calcination Before Test | K$_a$ |
|---|---|---|---|
| 3(b) | FAPO-5 | 600° C., 3 hrs. | 0.85 |
| 5(a) | FAPO-11 | 550°, 7 hrs. | 0.26 |
| 6(b) | FAPO-16 | 600° C., 2 hrs. | 0.6 |
| 7(b) | FAPO-17 | 600° C., 2 hrs. | 0.09 |
| 10(a) | FAPO-34 | 600° C., 1.25 hrs. | 0.6 |

The FAPO compositions of the present invention are, in general, hydrophilic and absorb water preferentially over common hydrocarbon molecules such as paraffins, olefins and benzenoid aromatic species, e.g., benzene, xylenes and cumene. Thus the present metal aluminophosphates as a class are useful as desiccants in such adsorption separation/purification processes as natural gas drying, and cracked gas drying. Water is also preferentially absorbed over the so-called permanent gases such as carbon dioxide, nitrogen, oxygen and hydrogen. These metal aluminophosphates are therefore suitably employed in the drying of reformer hydrogen streams and in the drying of oxygen, nitrogen or air prior to liquefaction. In this respect the absorptive properties of the present metal aluminophosphates appear to be quite similar to those of the low silica aluminosilicate zeolites, despite the fact that they exhibit, at best, a modest ion-exchange capacity.

The present FAPO compositions also exhibit novel surface selectively characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silica or alumina bases. Of the general class, those species having pores larger than about 5 A are preferred or catalytic applications.

Among the hydrocarbon conversion reactions catalyzed by FAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using FAPO catalyst compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The FAPO catalyst compositions employed in hydrocracking are also suitable for use in reforming processes in which the hydrocarbon feedstocks contact the catalyst at temperatures of from about 700° F. to 1000° F, hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (H/HC) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0, are suitable.

The unique crystal structure of the present FAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with FAPO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the FAPO catalytic in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts of hydrocracking. Consequently, it is necessary to operate at more extreme conditions when it is desired to obtain the same degree of hydrocracking conversion per pass on a relatively nitrogenous feed than are required with a feed containing less organonitrogen compound. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking-inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptane and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred cation form is a combination of the FAPO with polyvalent metal compounds (such as sulfides) of metals of Group II-A, Group II-B and rare earth metals. For alkylation and dealkylation processes the FAPO compositions having pores of at least 5 A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation of benzene, toluene and xylene, the preferred alkylating agents are olefins such as ethylene and propylene.

We claim:

1. Crystalline ferroaluminophosphate having a three-dimensional microporous framework structure of $FeO_2$, $AlO_2$ and $PO_2$ tetrahedral units and having an empirical chemical composition on an anhydrous basis expressed by the formula $$mR:(Fe_xAl_yP_z)O_2$$ 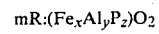

wherein "R" represents at least one organic templating agent present in the intracrystalline pore system; "m" represents the moles of "R" present per mole of $(Fe_xAl_yP_z)O_2$ and has a value of from zero to 0.3, "x", "y" and "z" represent the mole fraction of the iron, aluminum and phosphorus respectively present as tetrahedral oxides, said mole fractions being such that they are within the tetragonal compositional area defined by points A, B, C and D of the ternary diagram which is FIG. 1 of the drawings.

2. Crystalline ferroaluminophosphate according to claim 1 wherein the mole fractions of iron, aluminum, and phosphorus present as tetrahedral oxides are within the tetragonal compositional area defined by the points a, b, c and d of the ternary diagram which is FIG. 2 of the drawings.

3. Composition according to claim 1 wherein "m" has a value of from 0.02 to 0.03.

4. Crystalline ferroaluminophosphate according to claim 1 or claim 2 having a characteristic X-ray powder diffraction pattern which contains at least the d-spacings set forth in Table I.

5. Crystalline ferroaluminophosphate according to claim 1 or claim 2 having a characteristic X-ray powder diffraction pattern which contains at least the d-spacings set forth in Table III.

6. Crystalline ferroaluminophosphate according to claim 1 or claim 2 having a characteristic X-ray powder diffraction pattern which contains at least the d-spacings set forth in Table V.

7. Crystalline ferroaluminophosphate according to claim 1 or claim 2 having a characteristic X-ray powder diffraction pattern which contains at least the d-spacings set forth in Table VII.

8. Crystalline ferroaluminophosphate according to claim 1 or claim 2 having a characteristic X-ray powder diffraction pattern which contains at least the d-spacings set forth in Table IX.

9. Crystalline ferroaluminophosphate according to claim 1 or claim 2 having a characteristic X-ray powder diffraction pattern which contains at least the d-spacings set forth in Table XI.

10. Crystalline ferroaluminophosphate according to claim 1 or claim 2 having a characteristic X-ray powder diffraction pattern which contains at least the d-spacings set forth in Table XIII.

11. Process for preparing a crystalline ferroaluminophosphate of claim 1 which comprises providing a reaction mixture composition expressed in terms of molar oxide ratios as follows:

$$aR_2O:(Fe_xAl_yP_z)O_2:bH_2O$$

wherein "R" is an organic templating agent; "a" has a value great enough to constitute an effective concentration of "R" and is within the range of greater than zero to 3; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value of at least 0.01, and being within the hexagonal compositional area defined by points E, F, G, H, I, and J which is FIG. 3 of the drawings and maintaining said reaction mixture under conditions whereby crystals of said ferroaluminophosphate are formed.

12. Process according to claim 11 wherein the source of phosphorus in the reaction mixture is orthophosphoric acid.

13. Process according to claim 11 wherein the source of phosphorus in the reaction mixture is orthophosphoric acid and the source of aluminum is at least one compound selected from the group of pseudo-boehmite and aluminum alkoxide.

14. Process according to claim 13 wherein the aluminum alkoxide is aluminum isopropoxide.

15. Process according to claim 11 wherein the organic templating agent is a quaternary ammonium or quaternary phosphonium compound having the formula $$R_4X^+$$

wherein X is nitrogen or phosphorus and each R is an alkyl or aryl group containing from 1 to 8 carbon atoms.

16. Process according to claim 11 wherein the organic templating agent is an amine.

17. Process according to claim 11 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-diethylethanolamine; choline; N,N'-dimethylpiperazine; 1,4-diazabicyclo-(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; tetramethylammonium ion; tetrabutylammonium ion; tetrapentylammonium ion; di-n-butylamine; neopentylamine; di-n-pentylamine; isopropylamine; t-butylamine; ethylenediamine, pyrrolidine, 2-imidazolidone; di-n-propylamine; and a polymeric quaternary ammonium salt $[(C_{14}H_{32}N_2)]_x^+$ wherein x is a value of at least 2.

18. Crystalline ferroaluminophosphate prepared by calcining a composition of claim 1 or claim 2 or claim 3 to a temperature sufficiently high to remove at least some of the organic templating agent present in the intracrystalline pore system.

19. Crystalline ferroaluminophosphate prepared by calcining a composition of claim 1 or claim 2 at a temperature sufficiently high to remove at least some of the organic templating agent present in the intracrystalline pore system, said ferroaluminophosphate composition prior to said calcining having a characteristic X-ray powder diffraction pattern which contains at least the d-spacings set forth in Table I or Table III or Table V or Table VII or Table IX or Table XI or Table XIII.

* * * * *